United States Patent [19]

Gates et al.

[11] 4,263,037

[45] Apr. 21, 1981

[54] 5-CYANO-2,3-DIHYDROBENZOFURANS USEFUL AS HERBICIDES

[75] Inventors: Peter S. Gates; Derek Baldwin, both of Cambridge; Carol A. Wilson, Saffron Walden; John Gillon, Cambridge, all of England

[73] Assignee: Fisons Limited, London, England

[21] Appl. No.: 62,511

[22] Filed: Jul. 27, 1979

[30] Foreign Application Priority Data

Jul. 29, 1978 [GB] United Kingdom ............... 31646/78
Oct. 24, 1978 [GB] United Kingdom ............... 41982/78

[51] Int. Cl.$^3$ .................... A01N 43/08; C07D 307/83
[52] U.S. Cl. ........................................... 71/88; 71/91; 71/94; 71/95; 544/163; 546/196; 549/10; 260/326.34; 260/340.3; 260/343.3 R; 260/346.22; 260/346.73; 260/465 D; 260/465 E; 260/465 F
[58] Field of Search ...................... 260/346.22, 346.73; 71/88

[56] References Cited

U.S. PATENT DOCUMENTS 4,162,154   7/1979   Gates et al. .................... 260/346.22

Primary Examiner—Henry R. Jiles
Assistant Examiner—Bernard Dentz
Attorney, Agent, or Firm—Wenderoth, Lind & Ponack

[57] ABSTRACT

The invention provides herbicidally-active 2,3-dihydro-5-cyanobenzofurans of the formula:

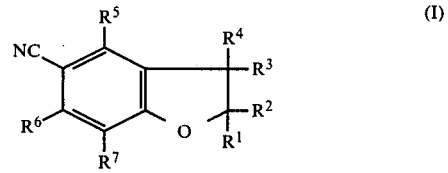

(I)

(wherein: $R^1$ and $R^2$ together represent =O or $R^1$ represents hydrogen and $R^2$ represents hydrogen, hydroxy, alkoxy, acyloxy, alkoxycarbonyloxy, alkylthiocarbonyloxy, halogen, isothiocyanato, amino, alkylamino, dialkylamino, arylamino, acylamino, alkoxycarbonylamino, alkylthiocarbonylamino, N-bonded heterocyclyl, cyano or alkylthio; $R^3$ and $R^4$ together represent alkylene or each represent hydrogen or alkyl; and $R^5$, $R^6$ and $R^7$, which may be the same or different, each represent hydrogen, halogen, alkyl, alkoxy, acyl or cyano), processes for their preparation and herbicidal compositions containing them.

7 Claims, No Drawings

5-CYANO-2,3-DIHYDROBENZOFURANS USEFUL AS HERBICIDES

This invention concerns herbicidally-active compounds, processes for their preparation, intermediates obtained in those processes, and compositions containing said herbicidally active compounds.

In one aspect this invention provides the 2,3-dihydro-5-cyanobenzofurans of the formula:

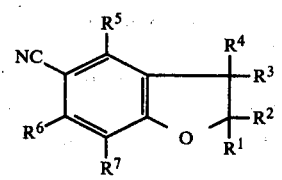

wherein: $R^1$ and $R^2$ together represent =O or $R^1$ represents hydrogen and $R^2$ represents hydrogen, hydroxy, alkoxy, acyloxy, alkoxycarbonyloxy, alkylthiocarbonyloxy, halogen, isothiocyanato, amino, alkylamino, dialkylamino, arylamino, acylamino, alkoxycarbonylamino, alkylthiocarbonylamino, N-bonded heterocyclyl, cyano or alkylthio; $R^3$ and $R^4$ together represent alkylene or each represent hydrogen or alkyl; and $R^5$, $R^6$ and $R^7$, which may be the same or different, each represent hydrogen, halogen, alkyl, alkoxy, acyl or cyano.

The term 'alkyl' used alone or in cognate expressions, e.g. alkoxy, is used herein to include both unsubstituted or substituted alkyl groups. Where such a group is substituted, it is preferably substituted by one or more hydroxy, alkoxy or alkylthio groups or halogen atoms. The term 'alkyl' is also used herein to include straight and branched-chain alkyl groups and cycloalkyl groups.

The term 'acyl' is used herein to include alkanoyl, substituted alkanoyl, benzoyl, alkenoyl, carbamoyl, alkylcarbamoyl, phenylcarbamoyl, dialkylcarbamoyl and alkylsulphonyl groups.

When $R^2$ represents alkoxy, the alkyl moiety thereof is preferably of 1 to 6 carbon atoms, especially of 1 to 4 carbon atoms, for example methoxy, ethoxy, n-propoxy, isopropoxy, n-butoxy or isobutoxy.

When $R^2$ represents acyloxy, any alkyl moiety thereof is preferably of 1 to 6, especially of 1 to 4, carbon atoms, and any alkenyl moiety thereof is preferably of 2 to 6, especially 2 to 4, carbon atoms. Specific preferred acyloxy groups which $R^2$ may represent include acetoxy, chloracetoxy, propanoyloxy, n-butanoyloxy, n-pentanoyloxy, isobutanoyloxy, isopentanoyloxy, propenyloxy, carbamoyloxy, methylcarbamoyloxy, phenylcarbamoyloxy, dimethylcarbamoyloxy and methylsulphonyloxy.

When $R^2$ represents halogen, it may for example be bromine or iodine, but is preferably chlorine.

When $R^2$ represents alkylamino or dialkylamino, the or each alkyl moiety thereof is preferably of 1 to 6 carbon atoms, especially of 1 to 4 carbon atoms, e.g. methylamino, ethylamino or dimethylamino.

When $R^2$ represents arylamino, the aryl moiety thereof is preferably phenyl.

When $R^2$ represents acylamino, any alkyl moiety thereof is preferably of 1 to 6, especially of 1 to 4, carbon atoms, specific preferred groups being acetylamino, propionylamino, methylsulphonylamino, N-methyl-N-sulphonylamino, ureido, 3-methylureido, 3,3-dimethylureido and 1,3,3-trimethylureido.

When $R^2$ represents alkoxycarbonyloxy, alkylthiocarbonyloxy, alkoxycarbonylamino or alkylthiocarbonylamino, the alkyl moiety thereof is preferably of 1 to 6, especially 1 to 4, carbon atoms, specific preferred groups being methoxycarbonyloxy, methylthiocarbonyloxy, methoxycarbonylamino, methylthiocarbonylamino and N-methyl-N-methylthiocarbonylamino.

When $R^2$ represents N-bonded heterocyclyl, it is preferably of 5 or 6 members, e.g. pyrrolidino, piperidino or morpholino.

When $R^2$ represents alkylthio, the alkyl moiety thereof is preferably of 1 to 6 carbon atoms, e.g. methylthio or ethylthio.

When $R^3$ and $R^4$ together represent an alkylene chain, it is preferably of 3 to 6 carbon atoms, especially tetramethylene or pentamethylene.

When $R^3$ and/or $R^4$ represents alkyl, however, it is preferably of 1 to 6, especially 1 to 4, carbon atoms, e.g. methyl, ethyl, n-propyl or isopropyl. It is desirably unsubstituted. When it is substituted, however, it may be substituted by one or more hydroxy groups or alkoxy or alkylthio groups of 1 to 4 carbon atoms or halogen atoms, e.g. 2-hydroxyethyl, 2-methoxyethyl, 2-methylthioethyl, chloromethyl or trifluoromethyl.

$R^3$ and $R^4$ are preferably together alkylene or both alkyl, especially identical alkyl (especially methyl) groups.

$R^5$, $R^6$ and $R^7$ independently preferably represent hydrogen. When one or more thereof is other than hydrogen, however, it is preferably alkyl of 1 to 6 carbon atoms (e.g. methyl or ethyl), chlorine, bromine, cyano, alkanoyl of 2 to 6 carbon atoms (e.g. acetyl) or alkoxy of 1 to 4 carbon atoms (e.g. methoxy or ethoxy).

Specific preferred compounds of formula I are those set out in the Examples hereinafter. Particular mention may be made however of the following:

5-cyano-2,3-dihydro-3,3-dimethylbenzofuran,
5-cyano-2,3-dihydro-3,3-dimethyl-2-hydroxybenzofuran,
5-cyano-2,3-dihydro-3,3-dimethyl-2-ethoxybenzofuran,
5-cyano-2,3-dihydro-3,3-dimethyl-2-chloroacetoxybenzofuran,
5-cyano-2,3-dihydro-3,3-dimethylbenzofuran-2-one,
5-cyanospiro[benzofuran-3(2H)-1'-cyclopentan]-2-one, and
5-cyanospiro[benzofuran-3(2H)-1'-cyclohexan]-2-one.

The compounds of formula I possess, when $R^1$ and $R^2$, or $R^3$ and $R^4$, are not identical, at least one asymmetric carbon atom. They may therefore exist as distinct stereoisomeric forms or as mixtures thereof. The activities of the stereoisomeric forms of a single compound may be different.

In another aspect, this invention provides a process for the preparation of a 2,3-dihydro-5-cyanobenzofuran of formula I which comprises subjecting a substituted 2,3-dihydro-benzofuran of the formula:

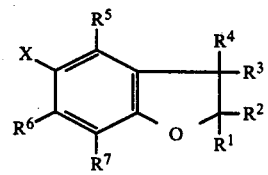

wherein: $R^1$, $R^2$, $R^3$, $R^4$, $R^5$, $R^6$ and $R^7$ are as defined hereinbefore and X represents a group convertible to or replaceable by cyano, to appropriate conditions to effect the conversion or replacement.

A number of methods of effecting replacement of the group X are available.

For example, X may represent a group such as halogen which is susceptible to nucleophilic displacement by cyanide. X may thus represent chlorine, bromine or iodine, and the reaction may be effected by means of cyanide ion in the presence of a transition metal compound catalyst, e.g. cuprous cyanide, preferably employed in a high boiling point solvent which is inert under the reaction conditions employed, for example dimethylformamide. The reaction is desirably effected at a temperature of from 100° to 250° C.

A number of methods also exist for converting the group X into a cyano group.

For example, X may represent a group which is dehydratable to a cyano group, e.g. —$CONH_2$ or —CH=NOH, and the compound of formula II is dehydrated to give the corresponding compound of formula I. The dehydration is conveniently effected by means of a dehydrating agent, for example an anhydride, e.g. acetic anhydride or phosphorus pentoxide, or a thionyl halide, e.g. thionyl chloride, and at a temperature of from 5° to 150° C.

The dehydration is conveniently effected in a suitable solvent medium, for example a hydrocarbon, e.g. benzene or toluene.

Alternatively, X may represent hydrogen, and the compound of formula II may be reacted with chlorosulphonylisocyanate in an inert, non-aqueous solvent, to give the desired compound of formula I. The reaction is desirably effected at a temperature of from 0° to 50° C.

Alternatively, X may represent amino, and the compound of formula II may be diazotised (e.g. by means of nitrous acid, e.g. sodium nitrite/acid) and is then reacted with cyanide ion (preferably cuprous cyanide) to give the desired compound of formula I.

Alternatively, X may represent carboxyl, and the compound of formula II may be converted to the corresponding amide and then dehydrated, or may be reacted directly with chlorosulphonylisocyanate to give the desired compound of formula I.

Alternatively, X may represent methyl, and the compound of formula II may be reacted with ammonia and oxygen in the presence of a transition metal compound catalyst to give the desired compound of formula I.

The reaction may be vapour phase or liquid phase, optionally in the presence of a solvent, e.g. benzonitrile. The catalyst is preferably manganous bromide.

The compounds of formula II wherein X represents halogen may be prepared by a process in which a corresponding 5-unsubstituted-2,3-dihydrobenzofuran is reacted with the appropriate halogen optionally or if necessary in the presence of a suitable halogen carrier as catalyst to give the desired compound.

The halogen carrier may preferably be an iron/iodine catalyst, especially where, as preferred, X represents bromine.

The reaction is desirably effected at a temperature of from 0° to 150° C., and preferably in the presence of a solvent, e.g. carbon tetrachloride or acetic acid.

The compounds of formula II wherein X represents —$CONH_2$ may be prepared by a process in which a corresponding 5-haloformyl-2,3-dihydrobenzofuran is reacted with ammonia to give the desired compound.

The reaction is desirably effected in aqueous solution and at a temperature of from 0° to 100° C.

The 5-haloformyl-2,3-dihydrobenzofurans used as starting materials in this process, which are preferably 5-chloroformyl-2,3-dihydrobenzofurans, may themselves be prepared by halogenation of the corresponding 5-carboxyl-2,3-dihydrobenzofurans. The halogenation is preferably effected by means of a thionyl halide, e.g. thionyl chloride or a phosphorus halide, e.g. phosphorus pentachloride, and desirably at a temperature of from 0° to 120° C., optionally in a suitable solvent, e.g. petroleum ether.

The 5-carboxyl-2,3-dihydrobenzofurans used as starting materials may themselves be prepared by a process in which a 5-halo-2,3-dihydrobenzofuran of formula II is reacted with carbon dioxide in the presence of magnesium to give the desired compound.

The reaction is desirably effected in a suitable solvent medium, for example an ether, e.g. diethyl ether, and at a temperature of from 0° to 40° C.

Alternatively, the 5-carboxyl-2,3-dihydrobenzofurans may be prepared by a process in which the corresponding 5-formyl-2,3-dihydrobenzofuran is oxidised to give the desired compound.

The oxidation is desirably effected by means of an oxidising agent, e.g. potassium permanganate or dichromate or silver oxide, or by a Cannizzaro reaction with concentrated alkali-metal hydroxide solution.

The 5-formyl-2,3-dihydrobenzofurans employed as starting materials may themselves be prepared by a process in which a corresponding 5-unsubstituted-2,3-dihydrobenzofuran is reacted with a suitable Vilsmeier reagent to give the desired compound.

The Vilsmeier reagent is preferably phosphorus oxychloride and dimethylformamide.

The reaction is desirably effected at a temperature of from 0° to 150° C.

The compounds of formula II wherein X represents —CH=NOH may be prepared from the corresponding 5-formyl-2,3-dihydrobenzofurans by reaction thereof with hydroxylamine to give the desired compound.

The reaction is preferably effected in an appropriate solvent medium, e.g. an alkanol such as ethanol, or water, and in the presence of a base, e.g. an alkali-metal carbonate or acetate, e.g. sodium acetate.

The compounds of formula II wherein X represents amino may be prepared by nitration of the corresponding 5-unsubstituted compound using a mild nitrating agent, e.g. cupric nitrate, followed by reduction of the formed 5-nitro-2,3-dihydrobenzofuran using a suitable reducing agent, e.g. sodium dithionite or stannous chloride.

The compounds of formula II wherein X represents methyl may be prepared by methods analogous to methods described hereinafter for the preparation of the corresponding 5-halo-2,3-dihydrobenzofurans by reaction of a p-substituted phenol or anisole of formula IV with an alkenyl halide of formula V.

In a further aspect, this invention provides a process for the preparation of a compound of formula I which comprises cyclising a compound of the formula:

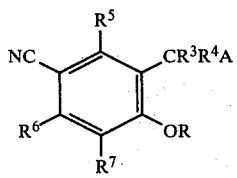

(III)

wherein $R^3$, $R^4$, $R^5$, $R^6$ and $R^7$ are as defined hereinbefore and A and R represent groups cyclisable to form a group —$CR^1R^2$— where $R^1$ and $R^2$ are as defined hereinbefore.

Several possibilities exist for the groups A and R depending on the desired group —$CR^1R^2$—. For example, R may represent hydrogen, alkyl (preferably of 1 to 6 carbon atoms, e.g. methyl or ethyl) or acyl (preferably of 2 to 6 carbon atoms, e.g. acetyl, chloroacetyl, propanoyl, n-butanoyl, isobutanoyl, n-pentanoyl, isopentanoyl or propenoyl), and A can represent:

(i) —$CH_2Hal$ (where Hal represents halogen, preferably chlorine), to give compounds of formula I where $R^1$ and $R^2$ both represent hydrogen, (ii) —CN, to give compounds of formula I where $R^1$ and $R^2$ together represent =O, or (iii) —CHO, to give compounds of formula I where $R^2$ represents hydroxy.

The cyclisations may be effected by means of an acid or base as desired, e.g. hydrochloric acid or sodium hydroxide.

Where R represents alkyl, a dealkylating agent is preferably present, for example pyridine hydrochloride (preferably employed in a high boiling point solvent, e.g. quinoline) or hydrobromic acid.

The compounds of formula III wherein A and R respectively represent —$CH_2Hal$ and hydrogen or alkyl may themselves be prepared by a process in which a compound of the formula:

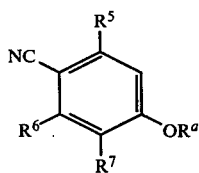

(IV)

(wherein $R^5$, $R^6$ and $R^7$ are as defined hereinbefore and $R^a$ represents hydrogen or alkyl) is reacted with an alkenyl halide of the formula:

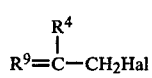

(V)

(wherein $R^4$ and Hal are as defined hereinbefore and $R^9$ represents an alkylidene group derived from a group $R^3$ as defined hereinbefore).

The reaction is preferably effected in the presence of an acid, e.g. a mineral acid, e.g. sulphuric acid.

The compounds of formula III wherein A and R respectively represent —CN and hydrogen or alkyl and at least one of $R^3$ and $R^4$ is other than hydrogen, may be prepared by a process in which a cyanomethylbenzene of the formula:

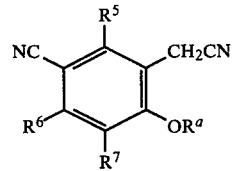

(VI)

(wherein X, $R^a$, $R^5$, $R^6$ and $R^7$ are as defined hereinbefore) is alkylated in the presence of a base by means of reagents of formula $R^3Y$ and $R^4Y$ (to give compounds wherein $R^3$ and $R^4$ are separate entities and are other than hydrogen) or of formula $Y(CH_2)_nY$ to give compounds wherein $R^3$ and $R^4$ together represent an alkylene chain), $R^3$ and $R^4$ being as defined hereinbefore, Y representing halogen and n representing an integer of from 3 to 6.

Y preferably represents bromine.

To obtain the compounds wherein $R^3$ and $R^4$ are different, the compound of formula VI should first be reacted with a molar proportion of $R^3Y$ to effect the first substitution, and then, if desired, with a molar proportion of $R^4Y$ to effect the second substitution. Naturally, if $R^3$ and $R^4$ in the desired compound are identical then the two substitutions may be effected at the same time.

The alkylations are desirably effected in an appropriate solvent medium, for example dimethylformamide.

The base employed may be any suitable strong base, for example sodium hydride.

The compounds of formula VI may themselves be prepared by a process in which the corresponding halomethylbenzene of the formula:

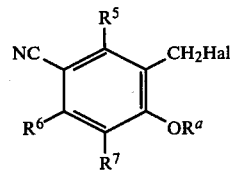

(VII)

(wherein $R^a$, $R^5$, $R^6$, $R^7$ and Hal are as defined hereinbefore) is subjected to nucleophilic displacement to give the desired compound.

The nucleophile employed is preferably an alkali-metal cyanide, for example sodium cyanide, in a suitable solvent, e.g. ethanol.

The compounds of formula III wherein A and R respectively represent —CHO and hydrogen or alkyl may be prepared by a process in which a corresponding compound of the formula:

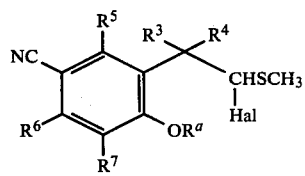

(VIII)

(wherein $R^a$, $R^3$, $R^4$, $R^5$, $R^6$, $R^7$ and Hal are as defined hereinbefore) is hydrolysed by means of an aqueous medium to give the desired compound.

The compounds of formula VIII may themselves be prepared by a process in which a methylthioethylbenzene of the formula:

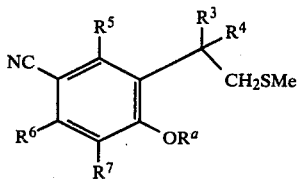

(IX)

(wherein $R^a$, $R^3$, $R^4$, $R^5$, $R^6$ and $R^7$ are as defined hereinbefore) is subjected to the action of a halogenating agent to give the desired compound.

The halogenating agent is preferably a chlorinating agent, desirably N-chlorosuccinimide, and is preferably employed in a suitable solvent medium, for example a chlorinated hydrocarbon e.g. carbon tetrachloride.

The methylthioethylbenzenes of formula IX may themselves be prepared by a process in which a compound of formula III where A and R respectively represent —CH$_2$Hal and hydrogen or alkyl is reacted with an alkali-metal salt of methanethiol to give the desired compound.

The alkali-metal salt is preferably the sodium salt, and the reaction is desirably effected in an appropriate solvent medium, e.g. dimethylformamide.

The compounds of formula III wherein R represents acyl may be prepared from the corresponding compounds wherein R represents hydrogen by reaction with an appropriate acylating agent.

The cyano componds of formulae III, IV, V, VI, VII, VIII and IX may alternatively be prepared by a process in which the corresponding compound containing at the appropriate position on the ring a group replaceable by cyano (e.g. halogen, especially bromine) is subjected to a replacement reaction with cyanide to give the desired compound.

The replacement is preferably effected by means of cuprous cyanide, preferably employed in a high boiling point solvent which is inert under the reaction conditions employed, for example dimethylformamide, dimethylacetamide or N-methylpyrrolidone. The reaction is desirably effected at a temperature of from 100° to 250° C.

The starting materials in this process may be prepared by processes analogous to those described hereinbefore for the preparation of the corresponding cyano compounds.

The compounds of formula I wherein $R^2$ represents alkoxy may be prepared by a process in which the corresponding compound of formula I wherein $R^2$ represents hydroxy or halogen is reacted with an appropriate alkanol in the presence of an acid catalyst, to give the desired compound.

The acid catalyst is desirably a mineral acid, e.g. sulphuric acid, and the reaction is preferably effected at a temperature of from 0° to 150° C.

The compounds of formula I wherein $R^2$ represents acyloxy or acylamino may be prepared by a process in which a corresponding compound of formula I wherein $R^2$ respectively represents (a) hydroxy or halogen or (b) amino or alkylamino is reacted with an appropriate acid, acyl halide or acid anhydride to give the desired compound.

The reaction is desirably effected in an appropriate solvent medium, e.g. an ether, e.g. diethyl ether, and in the presence of a base, e.g. a tertiary amine, e.g. triethylamine. The temperature of the reaction is preferably from 0° to 150° C.

The compounds of formula I wherein $R^2$ represents alkoxycarbonyloxy, alkylthiocarbonyloxy, alkoxycarbonylamino or alkylthiocarbonylamino may be prepared by analogous reaction between the appropriate compound of formula I where $R^2$ represents hydroxy, amino or alkylamino and an appropriate alkoxycarbonyl or alkylthiocarbonyl halide.

The compounds of formula I wherein $R^2$ represents halogen may be prepared by a process in which the corresponding compound of formula I wherein $R^2$ represents hydrogen is halogenated in the presence of a free-radical catalyst to give the desired compound.

The halogenation is preferably effected by means of the appropriate halogen.

The free radical catalyst may be light or a chemical catalyst e.g. 2,2'-azobisisobutyronitrile.

The halogenation is desirably effected in an appropriate solvent medium, e.g. a halogenated hydrocarbon, e.g. dichloromethane or carbon tetrachloride, and preferably at a temperature of from 50° to 150° C.

Alternatively, the compounds of formula I wherein $R^2$ represents halogen may be prepared by a process in which the corresponding compound of formula I wherein $R^2$ represents hydroxy is reacted with an appropriate halogenating agent, e.g. a thionyl halide, and in the presence of a base.

The base is preferably a tertiary organic base, e.g. pyridine, and the reaction is desirably effected in a suitable solvent, e.g. an ether or a chlorinated hydrocarbon, e.g. methylene chloride or carbon tetrachloride.

The temperature employed is preferably from 0° to 40° C.

The compounds of formula I wherein $R^2$ represents isothiocyanato may be prepared by a process in which the corresponding compound wherein $R^2$ represents halogen is reacted with an alkali-metal thiocyanate to give the desired compound.

The reaction is desirably effected in a suitable solvent medium, e.g. dimethylformamide, and at a temperature of from 50° to 150° C.

The compounds of formula I wherein $R^2$ represents hydroxy may of course be prepared by a process in which a corresponding compound wherein $R^2$ represents alkoxy, acyloxy or halogen is hydrolysed under appropriate conditions to give the desired compound.

The compounds of formula I wherein $R^2$ represents amino, alkylamino, dialkylamino, arylamino or N-bonded heterocyclyl may be prepared by a process in which a corresponding compound wherein $R^2$ represents halogen is reacted with the appropriate amine to give the desired compound.

The reaction is conveniently effected in the optional presence of an appropriate solvent medium, e.g. dimethylformamide or toluene, and at a temperature of from 50° to 150° C.

Similarly, the compounds of formula I wherein $R^2$ represents cyano may be prepared by a process in which a corresponding compound wherein $R^2$ represents halogen is reacted with cyanide ion in the presence of a transition metal compound catalyst to give the desired compound.

The cyanide ion is desirably provided by cuprous cyanide, and the reaction is desirably effected in a suitable solvent medium, e.g. dimethylformamide. The reaction is desirably effected at a temperature of from 60° to 160° C.

Similarly, the compounds of formula I wherein $R^2$ represents alkylthio may be prepared by a process in which a corresponding compound of formula I wherein $R^2$ represents halogen is reacted with the appropriate mercaptan or salt thereof to give the desired compound.

Where a salt of the mercaptan is employed it is preferably an alkali-metal salt thereof, e.g. the sodium or potassium salt thereof.

The reaction is desirably effected in a suitable solvent medium, e.g. dimethylformamide, and desirably at a temperature of from 20° to 150° C.

Certain intermediates in the above processes and derivatives thereof are herbicidally active, as are certain other compounds to which the compounds of formula I may be converted.

These herbicidally-active compounds particularly include those of the formula:

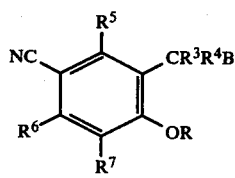

(X)

wherein $R^3$, $R^4$, $R^5$, $R^6$ and $R^7$ are as defined hereinbefore, R represents hydrogen, alkyl of 1 to 6 carbon atoms, alkanoyl (preferably of 2 to 6 carbon atoms) or alkenoyl (preferably of 2 to 6 carbon atoms), and B represents cyano, formyl, —CH$_2$Hal where Hal represents halogen, —CH$_2$OR$^{10}$ where $R^{10}$ represents a group as defined above for R, or —COM where M represents hydroxy, alkoxy (preferably of 1 to 6 carbon atoms), alkylamino (preferably of 1 to 6 carbon atoms), dialkylamino (each alkyl moiety of which is of 1 to 6 carbon atoms), phenylamino or alkylthio (preferably of 1 to 6 carbon atoms).

Where B represents a group A as defined hereinbefore, the compounds of formula X are of course also compounds of formula III.

Particular mention may be made of the compounds:
2-(5-cyano-2-propionyloxyphenyl)-2-methyl-1-propanal,
1-(5-cyano-2-hydroxyphenyl)cyclopentane carboxylic acid, and
1-(5-cyano-2-hydroxyphenyl)-1-dimethylcarbamoylcyclopentane.

Reduction of the compounds of formula I wherein $R^1$ represents hydrogen and $R^2$ represents hydroxy, or $R^1$ and $R^2$ together represent =O, gives the corresponding compounds of formula X where B represents —CH$_2$OH and R represents hydrogen.

The reduction is conveniently effected by means of an alkalimetal borohydride, e.g. sodium borohydride, and in an appropriate solvent medium, e.g. an alkanol such as methanol.

The compounds of formula X where B represents —CH$_2$OH and R represents hydrogen may be alkylated or acylated, if desired, to give further herbicidally active compounds of formula X where B represents —CH$_2$OR$^{10}$ and R and/or $R^{10}$ represents alkyl, alkanoyl or alkenoyl.

The alkylation or acylation may be effected for example by means of an appropriate halide, anhydride or alkyl or aryl isocyanate to give the desired alkyl or acyl group.

Where R and $R^{10}$ in the desired compound are different, the compound of formula X where B represents —CH$_2$OH and R represents hydrogen is reacted first with one molar proportion of the desired alkylating or acylating agent to give the corresponding compound of formula X wherein R represents hydrogen and $R^{10}$ represents the desired alkyl or acyl group, and then, if desired, with one molar proportion of a different alkylating or acylating agent to give the corresponding compound where $R^{10}$ and R are different and both are other than hydrogen.

Alternatively, a compound of formula III wherein R is other than hydrogen and A represents —CHO may be reduced (preferably by means of sodium borohydride) to give the corresponding compound of formula X where B represents —CH$_2$OH and R is as in the compound of formula III used as starting material.

Reaction of the compounds of formula I wherein $R^1$ and $R^2$ together represent =O with, as appropriate, an anion M or a compound MH where M represents hydroxy, alkoxy, alkylamino, dialkylamino, arylamino or alkylthio, gives the compounds of formula X where B represents a group —COM.

The compounds of the formula:

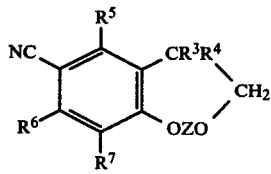

(XI)

(where $R^3$, $R^4$, $R^5$, $R^6$ and $R^7$ are as defined hereinbefore and Z represents a group of formula

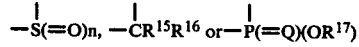

where n represents 1 or 2, $R^{15}$ and $R^{16}$, which may be the same or different, each represent hydrogen, alkyl, alkenyl, alkynyl, alkoxy, aryl, aryloxy, cyano or alkoxycarbonyl, or $R^{15}$ and $R^{16}$ together represent an oxygen or sulphur atom, an alkylene chain or an alkylimino or arylimino group, $R^{17}$ represents alkyl, and Q represents oxygen or sulphur) are also herbicidally active, and may all be prepared by appropriate techniques from the compounds of formula X wherein B represents —CH$_2$OH and R represents hydrogen by reaction thereof with a dihalide of formula Hal—Z—Hal (where Hal represents halogen) in the presence of a base if necessary or desired to give the desired compound.

The reaction is desirably carried out in an appropriate solvent or suspension medium, other than a dialkylamide, e.g. an aromatic hydrocarbon, e.g. toluene.

Alternatively, where Z represents a group —CR$^{15}$R$^{16}$— as defined hereinbefore, the dihalide may be replaced by a dialkoxy compound of formula $R^{18}O$—CR$^{15}R^{16}$—OR$^{18}$ (where $R^{18}$ represents an alkyl group, especially of 1-6 carbon atoms) in the presence of an acid catalyst, e.g. p-toluenesulphonic acid.

The compounds of formulae X and XI may all be prepared alternatively by displacing a group in a corresponding compound by cyano or by converting to cyano a group susceptible to such conversion. The displacement or conversion techniques employed may be analogous to those described hereinbefore in relation to compounds of formula I.

The compounds of formulae II, III, VI, VII, VIII, IX, X and XI, with the exception of those formula II where X represents hydrogen or alkyl, are themselves novel compounds, and this invention provides them per se, together with processes for their preparation as described hereinbefore.

The compounds of formulae I, III, X and XI, as stated before, are herbicidally active. These compounds are hereinafter referred to as the 'herbicidal compounds of the invention' or 'the present herbicidal compounds'.

In a further aspect, this invention provides a method of combating weeds at a locus infested or liable to be infested with them, which method comprises applying to the locus an effective amount of one or more herbicidal compounds of the invention.

The present herbicidal compounds are normally employed in the form of compositions, which can be prepared by admixing the ingredients. Usually the compositions are initially produced in the form of concentrates, e.g. containing 0.5–99%, desirably 0.5–85%, preferably 10 to 50%, by weight of the present herbicidal compounds, and these are diluted with water or hydrocarbon, usually water, for application, generally such that the concentration of the compound is 0.05–5%. Percentages and parts in this specification are by weight unless otherwise indicated.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant e.g. a polyhalogenated alkane such as dichlorodifluoromethane, and suitably also with a solvent.

A flowable suspension concentrate may be formed by grinding the compound with water, a wetting agent and a suspending agent.

Thus the present composition can for example be solid (e.g. dust or granules) and contain a solid carrier, or liquid (e.g. an emulsifiable concentrate) and contain a liquid carrier which may for example be a ketone or a hydrocarbon, for example xylene, which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The present herbicidal compounds, particularly those specifically identified herinbefore, and especially 5-cyano-2,3-dihydro-3,3-dimethylbenzofuran, 5-cyano-2,3-dihydro-3,3-dimethyl-2-hydroxybenzofuran, 5-cyano-2,3-dihydro-3,3-dimethyl-2-ethoxybenzofuran, 5-cyano-2,3-dihydro-3,3-dimethylbenzofuran-2-one, or 5-cyanospiro[benzofuran-3(2H)-1'-cyclopentan]-2-one, may be admixed with another pesticide, e.g. herbicide, insecticide or fungicide, or with a plant growth regulant or with a fertilizer. Particular advantages are obtained with mixtures with a second herbicide, e.g. one herbicide applied before planting or before emergence of a crop and the other herbicide applied after emergence of the crop.

The second herbicide employed in admixture or sequentially with the compounds of the present invention may be, for example, a substituted benzofuran herbicide, a phenoxyaliphatic acid, substituted urea, triazine, phenol, nitrile, bipyridylium compound, substituted benzoic acid, halogenated aliphatic acid, carbamate, thiocarbamate, chloroacetamide, diazine, arsenic compound or other herbicidal compound. In respect of selective herbicidal compositions for post-emergence use, the second herbicide is preferably a substituted phenoxyaliphatic acid; in respect of selective herbicidal compositions for pre-emergence use, the second herbicide is preferably a substituted benzofuran, a substituted urea or triazine.

The substituted benzofuran herbicide is preferably a compound of the formula:

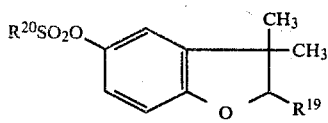

where $R^{19}$ represents alkoxy (especially ethoxy, propoxy or isopropoxy), and $R^{20}$ represents alkyl (especially methyl) or a group $R^{21}R^{22}N$— where $R^{21}$ and $R^{22}$, which may be the same or different, each represent hydrogen, alkyl (especially methyl) or carboxylic acyl (especially acetyl).

A particularly preferred substituted benzofuranyl compound for admixture with the compounds of the present invention, especially with those specifically identified herein, is 2-ethoxy-2,3-dihydro-3,3-dimethyl-benzofuran-5-yl methanesulphonate (common name ethofumesate).

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity.

The substituted urea generally comprises a tri- or tetra-substituted urea.

The triazine herbicide generally comprises a compound of the formula:

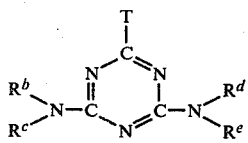

where T is a halogen or a group —$OR^f$ or —$SR^f$ where $R^f$ is an alkyl group, and $R^b$, $R^c$, $R^d$ and $R^e$ are hydrogen or alkyl.

Specific compounds with which the herbicidal compounds of the present invention, especially those specifically identified herein, may be admixed are as follows, all common names being as set out in the Pesticide Manual, 5th edition, issued by the British Crop Protection Council: alachlor, allidochlor, ametryne, aminotriazole (ATA), ancymidol, asulam, atrazine, aziprotryne, barban, benazolin, benfluralin, bensulide, bentazon, benthiocarb, bentranil, benzadox, benzoylpropethyl, benzthiazuron, bifenox, bromacil, bromofenoxim, bromoxynil, bromoxynil octanoate, brompyrazine, butachlor, buturon, butylate, carbetamide, chinonamid, chloramben, chloranocryl, chlorburomuron, chlorbufam, chlorfenac, chlorfenprop-methyl, chlorflurecol-methyl, chlormequat, chloroxuron, chlorphonium, chlorpropham, chlorthaldimethyl, chlorthiamid, chlortoluron, credazine, cyanazine, cycloate, cycluron, cyprazine, 2,4-D, dalapon, dalapon sodium, daminozide, 2,4-DB, delachlor, desmedipham, desmetryne, diallate, dicamba, dichlobenil, dichlorprop, dimethametryn, difenzoquat, difenzoquat methylsulphate, dimexan, dinitramine, dinoseb, dinoseb acetate, dinoterb, dinoterb acetate, diphenamid, dipropetryn, diquat, diuron, DNOC, DSMA, endothal, EPTC, erbon, ethiolate, EXD, fenoprop, fenuron, flamprop-isopropyl, fluometuron, fluorodifen, flumezin, flurecolbutyl, glyphosate, hexaflurate, ioxynil, ioxynil octanoate, isonoruron, isopropalin, isoproturon, karbutilate, lenacil, linuron, MCPA, MCPB, mecoprop, medinoterb acetate, merphos, methabenzthiazuron, methazole, methoprotryne, metobromuron, metoxuron, metribuzin, molinate, monalide, monolinuron, monuron, monuron-TCA, MSMA, naptopamide, naptalam, neburon, nitralin, nitrofen, norflurazon, noruron, oryzalin, paraquat, pebulate, pentanochlor, phenmedipham, phenmedipham-ethyl, phenobenzuron, picloram, piperophos, profluralin, prometon, prometryne, propachlor, propanil, propazine, propham, propyzamide, pyrazon, secbumeton, siduron, simazine, simetryne, sulfallate, swep, 2,4,5-T, 2,3,6-TBA, TCA, terbacil, terbucarb, terbumeton, terbuthylazine, terbutryne, thiafluron, triallate, trietazine, trifluralin, and vernolate, N-($\alpha$,$\alpha$-dimethylbenzyl)-N'-p-tolylurea, 3,4,5-tribromo-N,N-dimethylpyrazole-1-acetamide (U 27267), N-methyl-N-cyclohexyldithio-N'-o-fluorophenyl urea, N-benzoyl-N-(3,4-dichlorophenyl)-N',N'-dimethyl urea, ethyl N,N-diisobutylthiocarbamate, 4-(methylsulphonyl)-2,6-dinitro-N,N-dipropylaniline, 5(6)-chloro-2-isopropylbenzimidazole, 1-(3,4-dichlorophenyl)-3-methyl-2-pyrrolidinone, N-(p-bromophenyl)-N'-methyl-N'-methoxyurea, 3-(2,4-dichlorophenyl)-5-t-butyl-1,3,4-oxadiazol-2-one, N-(3,4-dichlorophenyl)-cyclopropanecarboxamide, 2,3,5-trichloro-4-pyridinol, 2-chloro-isopropylacetanilide, 2,6-dichlorothiobenzamide, 1,1'-bis(3,5-dimethylmorpholincarbonylmethyl)-4,4'-bipyridylium dichloride, sodium cis-3-chloroacrylate, 4,5,7-trichloro-2,1,3-benzthiadiazole, N-(3-chloro-4-methylphenyl)-2-methylpentanamide, n-propyl ethyl-n-butylthiolcarbamate, 3,4-dichloropropionanilide, N-cyclooctyl-N'-N'-dimethylurea, butyl m-chlorophenylcarbamate, 2-chloro-N-(1,3-dioxolan-2-ylmethyl)-2',6'-dimethylacetanilide, tetrahydrofurfuryl isothiocyanate, N-chloroacetyl-N-(2,6-diethylphenyl)-glycine isopropyl ester, N-chloroacetyl-N-(2,6-diethylphenyl)-glycine ethyl ester, N-chloroacetyl-N-(2-methyl-6-ethylphenyl)-glycine isopropyl ester, (1-methylethyl-O-methyl-O-(4-methyl-2-nitrophenyl)-phosphoramidothioate, 1,1-dimethylhexahydropyridazinum bromide, dimethylpiperidinium chloride, 1-[2-(2,4-dichlorophenyl)-1,3-dioxolan-2-methyl-]imidazole, 3'-(trifluoromethyl)phthalanilic acid, 3,6-dichloropropiocolinic acid, benzyl 3,5-dichloro-2,6-difluoro-4-pyridyl ether, ethyl N-(2,4-dichlorophenyl)-N-(trifluoromethanesulphonyl)-carbamate, N-(p-chlorophenyl)-N-(trifluoromethanesulphonyl)-carbamate, N-(p-chlorophenyl)-3,4,4,6-tetrahydrophthalimide, tributyl[(5-chloro-2-thienyl)-methyl]phosphonium chloride, N-pyrrolidinosuccinamic acid, methyl-3,6-dichloro-o-anisate, ethyl 5(4-chlorophenyl)-2-H-tetrazol-2-yl acetate, 2-(4-ethylamino-6-methylthio-s-triazin-2-yl)-amino-2-methylpropionitrile, 3-cyclohexyl-6-dimethylamino-1-methyl-1,3,5-triazine-2,4-(1H,3H)-dione, 1-(N-ethyl-N-propylcarbamoyl)-3-propyl-sulphonyl-1H-1,2,4-triazole, N-ethyl-N-(2-methyl-2-propenyl)-2,6-dinitro-4-(trifluoromethyl)-benzenamine, 2-ethyl-6-methyl-N(1'-methyl-2'-methoxyethyl)-chloro-acetanilide, 2-(3-chlorophenoxy)-propionic acid, N-n-propyl-N-cyclopropylmethyl-4-trifluoromethyl-2,6-dinitroaniline, N-benzyl-N-isopropyl-3,5-dimethylbenzamide, N-phenyldiethanolamine-bis(2-methoxy-3,6-dichlorobenzoate), [(3,5,6-trichloro-2-pyridinyl)oxy]-acetic acid, 3,3a-dihydro-2-(p-methoxyphenyl)-8H-pyrazolo-5,1-a-isoindol- 8-one, r-2-ethyl-5-methyl-c-5-(2-methylbenzyloxy)-1,3-dioxane, 3-(1-N-ethoxyamino)-propyliden-6-ethyl-3,4-dihydro-2H-pyran-2,4-dione, N-(5-n-butylsulphonyl-1,3,4-thiadiazolyl)-N-N'- dimethyl urea, 1,1-dimethyl-3-(m-chloro-p-trifluoromethoxyphenyl)urea, 2',6'-dimethyl-N-(2-methoxyethyl)-2-chloroacetanilide, 1-(α,α-dimethylbenzyl)-3-methyl-3-phenyl urea, 1-(o-fluorophenyl)-3-methyl-5-imidohydantoin, N-methyl-N-2-chlorocyclohexylthio-N'-(2-fluorophenyl) urea, 1-(3,4-dichlorophenyl)-3-methyl-3-(1-formyloxy-2,2,2-trichloroethyl)-urea, N-methyl-N-cyclohexyldithio-N'-o-fluorophenyl urea, N-carboxymethoxymethyl-2,6-diethyl-chloroacetanilide, 6-t-butyl-4,5-dihydro-3-isopropylpyridino-[4,5-c]isothiazol-4-one, 6-t-butyl-4,5-dihydro-3-isopropylpyrimidino-[5,4d]-isoxazol-4-one, O-(5-chloro-1-isopropyl-1,2,4-triazol-3-yl) O,O-diethylphosphorothioate, 2,4-dichlorophenyl 3-methoxy-4-nitrophenyl ether, 2-ethyl-5-methyl-5-(2-methylbenzyloxy)-1,3-dioxan, N-(1-ethylpropyl)-2,6-dinitro-3,4-xylidine, hexafluoroacetone trihydrate, methyl tetrachloro-N-methoxy-N-methylterephthalamate, S,S,S-tributyl phosphorotrithioate, N-sec-butyl-2,6-dinitro-3,4-xylidine, N,N-dimethyl-2-(3,4,5-tribromo-1-pyrazolyl)-propionamide, α(2,2,2-trichloroethyl)-styrene, 2-isopropyl-5-methyl-5-(2-methylbenzyloxy)1,3-dioxane, O-(methylsulphamoyl)-N,N-hexamethyleneglycollamide, O-(methylsulphamoyl)-N-isopropylglycollanilide, isobutyl 2-[4-(4-chlorophenoxy)-phenoxy]-propionate, methyl 2-[4-(2,4-dichlorophenoxy)-phenoxy]-propionate, 6-chloto-2-trifluoromethylimidazo-(4,5-b)pyridine, pentachlorophenyl, N'-p-chlorophenyl-O,N,N-trimethylisourea, 2-chloro-N-(but-1-yn-3-yl)-acetanilide, 2-bromo-2'-methyl-6'-t-butylacetanilide, 2-bromo-N-(methoxymethyl)-2'-methyl-6'-t-butyl-acetanilide, 2-chloro-N-(ethoxycarbonyloxymethyl)-2',6'-diethyl-acetanilide, O-(isopropylsulphamoyl)-N-(but-1-yn-3-yl)-glycollanilide, ethylene glycol bis-(trichloroacetate), hexachloroacetone, potassium cyanate, sodium chlorate, sodium metaborate, trichlorobenzyl chloride, undecylenic acid, N-(1-ethylpropyl)-3,4-dimethyl-2,6-dinitrobenzeneamine, tris(2-methoxyethoxy)-2'-chloroethylsilane, N-[2,4-dimethyl-5[[(trifluoromethyl)sulphonyl]-amino]-phenyl]-acetamide, 6-t-butyl-4-isobutylideneamino-3-methylthio-1,2,4-triazin-5(4H)-one, S-(4-methoxybenzyl-N,N-diethylcarbamothioate, 2-chloro-1-(3-ethoxy-4nitrophenoxy)-4-trifluoromethylbenzene, 3-(3-chloro-4-trifluoromethoxyphenyl)-1,1-dimethyl urea, N-isobutyl-2-oxoimidazolidine-1-carboxamide, O-ethyl O-(3-methyl-6-nitrophenyl)-N-sec-butyl-phosphorthioamidate, 2,6-dichlorobenzyl (2,2-dimethyl-4-ethyl-dioxolan-4-yl)methyl ether, 3',5'-dinitro-4-(di-n-propylamino)-acetophenone, N-chloroacetyl-N-(2,6-diethylphenyl) glycine ethyl ester, 2,3:4,6-di-O-isopropylidene-2-keto-L-fulonate, 1-m-trifluoromethylphenyl-4-dimethylamino-5-chloropyridazone, 4-amino-3-methyl-6-phenyl-1,2,4-triazin-5-(4H)-one, N-(2-methoxy-1-methylethyl)-2'-ethyl-6'-methyl-2-chloroanilide, O-(N-phenylcarbamoyl)-propane oxime, N-(4-methyl-3-(trifluoromethylsulphonylamino)phenyl)acetamide, 2,2,3,3-tetrafluoropropionic acid, O-methyl O-(4-methyl-2-nitrophenyl) (1-methylethyl)phosphoramidothioate, N-benzyl-N-isopropyl-3,5-dimethylbenzamide, 2-chloro-6-(2 -cyano-1-methyl-ethylamino)-4-cyclopropylamino-s-triazine, 2,2-dimethyl-N-benzyl-N-isopropylpropionamide, 3-[5-(1,1-dimethylethyl)-1,3,4-thiadiazol-2-yl]-4-hydroxy-1-methyl-2-imidazolidinone, N-(3-chloro-4-ethoxyphenyl)-N',N'-dimethylurea, 1-methyl-4-phenyl-pyridinium chloride, N-[5-(2-chloro-1,1-dimethylethyl)-1,3,4-thiadiazol-2-yl]cyclopropane carboxamide, 4-t-butyl-N-s-butyl-2,6-dinitroaniline, 1,1'-di(diethylcarbamoylmethyl)-4,4'-bipyridylium dichloride, 2-t-butyl-4-(3,3-dimethylureido)phenyl)-1,3,4-oxadiazolin-5-one, 2',6'-dimethyl-N-(2-methoxyethyl)-2-1H-1,2,4-triazole-1-carboxamide, tris-(2-methoxyethyl)-2'-chloroethylsilane, N-ethyl-N-(2-methyl-2-propenyl)-2,6-dinitro-4-(trifluoromethyl)aniline, N-(2-chloroethyl)-2,6-dinitro-N-propyl-4-(trifluoromethyl)aniline, methyl N-benzoyl-N-(3-chloro-4-fluorophenyl)-2-aminopropionate, 2,4-dichloro-6-fluorophenyl 4-nitrophenyl ether, N-3-(1',1',2',2'-tetrafluoroethoxy)phenyl-N',N'-dimethylurea, 1-methyl-3-phenyl-5-[3-(trifluoromethyl)phenyl]-4-(1H)-pyridinone, 2-amino-4-isopropylamino-6-chloropyrimidine, 6-t-butyl-4-isobutylideneamino-3-methylthio-1,2,4-triazin-5-(4H)-one, α-(4-chlorophenyl-α-(1-methylethyl)-5-pyrimidinemethanol, 2-(2,4,5-trichlorophenoxy)ethanol, 2-chloroethyl-tris(methoxy)-silane+α,ω-bis(2-chloroethyl)-α,α,ω-tetramethoxypoly[(2-chloroethyl)methoxy]siloxane, O-ethyl O-(3-methyl-6-nitrophenyl) N-s-butylphosphorothioamidate, N-(2'-methoxy-1'-methylethyl)-2'-ethyl-6'-methyl-2-chloro-acetanilide, N-(2-methyl-2-propenyl)-2,6-dinitro-N-propyl-4-(trifluoromethyl) aniline, N-(1-phenyl-5-bromo-6-oxopyridazin-4-yl) oxamic acid sodium salt, 1,1,1-trifluoro-N-[2-methyl-4-(phenylsulphonyl)-phenyl]methane sulphonamide, 3-ethoxycarbonylaminophenyl N-phenylcarbamate, ammonium ethyl carbamoylphosphonate, 1-allyl-1-tetrahydrogeranylpiperidinium bromide, N-((4-(dipropylamino)-3,5-dinitrophenyl)-sulphonyl)-S,S-dimethylsulphilimine, 2-chloro-N-(1-methyl-2-propynyl)acetanilide, N-(5-butylsulphonyl-1,3,4-thiadiazol-2-yl)-N,N'-dimethylurea, 1,3-dimethyl-1-(5-dimethylsulphamoyl-1,3,4-thiadiazol-2-yl)urea, 1-(5-ethylsulphonyl-1,3,4-thiadiazol-2-yl)-1,3-dimethylurea, 1-(5-t-butyl-1,3,4-thiadiazol-2-yl)-1,3-dimethylurea, N-(butoxymethyl)-2-chloro-N-(2-(1,1-dimethylethyl)-6-methyl-phenyl)acetamide, 3-(3-chloro-4-chlorodifluoromethyl-thiophenyl)-1,1-dimethylurea, [(3,5,6-trichloro-2-pyridinyl)oxy] acetic acid, 2-[4-(4-trifluoromethylphenoxy)-phenoxy)]propionic acid methyl ester, and 3-cyclohexyl-6-(dimethylamino)-1-methyl-s-triazine-2,4-(1H,3H)dione.

The invention also provides a two-container pack in which one or more herbicidal compounds of the invention are provided in a first container and one or more further pesticides, plant growth regulants or fertilizers are provided in a second container, especially in relative proportions as described hereinafter. Desirably, the two-container pack bears or contains instructions, either separate or in conjunction with one of the containers, for mixing the contents of the containers or separately applying the contents thereof.

The ratio by weight of the herbicidal compound(s) of the invention to the second herbicide may vary over a wide range according to the particular compounds employed and the intended use. In general, however, the ratio by weight of the herbicidal compound(s) of the invention to the second herbicidal component will be from 10:1 to 1:15, more preferably from 5:1 to 1:5, and especially from 3:1 to 1:3.

The herbicidal compounds of the invention may, if desired, be employed in admixture with non-phytotoxic oils.

The present herbicidal compound may, if desired, be employed in association with a herbicidal antidote (a substance having the property of improving the safety to crops of the compounds), e.g. N,N-diallyl-2,2-dichloroacetamide, 4'-chloro-2-hydroxyiminoacetanilide or 1,8-naphthalic anhydride. Although the antidote may be applied in admixture with the active compound, it is more preferably applied separately, and especially as a treatment for the crop seeds. The ratio by weight of herbicide to antidote is preferably from 1:2 to 8:1.

The herbicidal compounds of the invention are of herbicidal activity, and may be applied to plants, the soil, land or aquatic areas. They are of especial use as selective herbicides in crops, e.g. cotton, ryegrass, safflower, sorghum, millets, sunflowers, tobacco, or a food crop such as cereals, sugar beets, peas, beans (e.g. navy beans, soya beans and field beans), carrots, peanuts, maize, rice and potatoes. They may be applied pre- or post-planting of the crop, and may be employed post-emergence or preferably pre-emergence. When used in cereals, they are preferably applied with one or more plant-growth hormones. The compounds are of particular use in combating wild oats, blackgrass, crabgrass and nutsedges, especially in cereal crops.

The herbicidal compounds of the invention are preferably applied in an amount in total of from 0.1 to 20 kg/ha, more preferably 1 to 10 kg/ha, especially 2.5 to 8 kg/ha.

The invention will now be further described, though only by way of illustration, in the following Examples, in which all 'parts' are by weight.

EXAMPLE 1

5-Cyano-2,3-dihydro-3,3-dimethylbenzofuran (I)

(a) 2,3-Dihydro-3,3-dimethylbenzofuran

β-methallyl chloride (181 g 2.0 moles) was added dropwise over 1 hour to a mixture of phenol (470 g, 5.0 moles) and sulphuric acid (98 g, 1.0 mole) with vigorous stirring at 32°–8° C. After stirring for ½ hour at about 30° C. the solution was taken into ether, washed twice with water, dried over magnesium sulphate and run down under vacuum with the minimum of heat. The residue was immediately added to aqueous sodium hydroxide (2000 ml, 20%) and the mixture was stirred for 17 hours at room temperature. Extraction of the alkali-insoluble oil with ether, washing the ethereal solution with water (twice), drying over magnesium sulphate and running down yielded 170 g of crude product. Distillation gave two fractions (i) 105 g bp 91°–6° C. at 25 mm which was title product containing a trace of 2,3-dihydro-2,2-dimethylbenzofuran; (ii) 30.4 g bp 120°–5° C. at 28 mm which was mainly title product plus about 30% 2,2-dimethyl isomer.

(b) 2,3-Dihydro-3,3-dimethylbenzofuran-5-carboxaldehyde

Phosphorus oxychloride (30.6 g, 0.2 mole) was added dropwise to a mixture of dimethyl formamide (14.6 g, 0.2 mole) and 2,3-dihydro-3,3-dimethyl benzofuran (14.8 g, 0.1 mole) over half an hour. The temperature rose to 55° C. during addition. The temperature was then raised to 100° C. and maintained for 1 hour prior to addition to a hot solution of sodium acetate (75 g) in water (75 ml). After cooling, the organic layer was separated, dried and distilled yielding 5.6 g unchanged starting material bp 35°–40° C. at 0.1 mm and 5.2 g aldehyde bp 85° C. at 0.1 mm. The product contained a little 2,2-dimethyl isomer from the previous stage.

(c) 2,3-Dihydro-3,3-dimethylbenzofuran-5-carbaldoxime

A mixture of 2,3-dihydro-3,3-dimethylbenzofuran-5-carboxaldehyde (16 g, 0.091 mole), hydroxylamine hydrochloride (6.6 g, 0.095 mole), sodium acetate (7.8 g, 0.095 mole), ethanol (60 ml) and water (60 ml) was boiled under reflux for ¾ hour. The mixture was then added to ice-water and the precipitated solid was filtered off and dried. Recrystallisation from petroleum ether (bp 80°–100° C.), gave 7.7 g title oxime mp 91° C.

$C_{11}H_{13}NO_2$ requires: C, 69.09; H, 6.85; N, 7.33. Found: C, 68.99; H, 7.01; N, 7.74%.

(d) 5-Cyano-2,3-dihydro-3,3-dimethylbenzofuran (I)

2,3-Dihydro-3,3-dimethylbenzofuran-5-carbaldoxime (6 g, 0.031 mole) and acetic anhydride (6.4 g) were heated under reflux for 1 hour. The mixture was then added to ice-water and the precipitated brown solid filtered off. The solid was taken up in ether and the solution washed with aqueous sodium bicarbonate and water, dried over magnesium sulphate and run down. The residue was recrystallised from petroleum ether (bp 60°–80° C.) with charcoaling, yielding 3.0 g title product as pale yellow needles mp 70°–1° C.

$C_{11}H_{11}NO$ requires: C, 76.27; H, 6.40; N, 8.09. Found: C, 76.47; H, 6.41; N, 7.69%.

EXAMPLE 2

5-Cyanospiro[benzofuran-3(2H)-1'-cyclopentan]-2-one (I)

(a) 5-Bromospiro[benzofuran-3(2H)-1'-cyclopentan]-2-one (II)

1-Cyano-1-(2-methoxy-5-bromophenyl)-cyclopentane (prepared by reaction of 2-methoxy-5-bromobenzyl cyanide and sodium hydride, followed by reaction with 1,4-tetramethylenedibromide) (20 g) was heated under reflux in hydrobromic acid (48% aqueous, 150 ml) with stirring for 9½ hours. The reaction mixture was then cooled, diluted with water and the product extracted into ether. The ether solution was washed with water and dried over magnesium sulphate. Running down gave an orange oil which solidified on standing. Attempted crystallisation from petroleum ether (b.p. 60°–80° C.) gave a sticky orange solid which was chromatographed on alumina in ether. Work-up of the ether solution gave 12 g (63%) yellow solid which was shown to be crude product by NMR. Recrystallisation of a sample from petroleum ether (b.p. 60°–80° C.) gave a solid m.p. 103°–5° C.

(b) 5-Cyanospiro[benzofuran-3(2H)-1'-cyclopentan]-2-one (I)

5-Bromo-spiro-[benzofuran-3(2H)-1'-cyclopentan]-2-one (12 g, 0.045 mole) was heated under reflux in dimethyl formamide (15 ml) with cuprous cyanide (5.4 g, 0.06 mole) for 4 hours. The mixture was then cooled and sodium cyanide (12 g) in water (50 ml) added with stirring. After 10 minutes the precipitated brown solid was separated by filtration. Recrystallisation with charcoaling from ethanol gave the title product, 3.5 g (37%) m.p. 151°–2° C.

$C_{13}H_{11}NO_2$ requires: C, 73.22; H, 5.20; N, 6.57. Found: C, 72.79; H, 5.16; N, 6.34%.

EXAMPLE 3

5-Cyano-2,3-dihydro-3,3-dimethylbenzofuran-2-one (I)

(a) 2-Methoxy-5-bromo-α,α-dimethylbenzylcyanide

2-Methoxy-5-bromobenzyl cyanide (prepared by reaction of 2-methyl-4-bromoanisole, benzoyl peroxide and bromine, followed by reaction with sodium cyanide) (47 g, 0.208 mole) in dimethyl formamide (100 ml) was added cautiously to a cooled, stirred mixture of sodium hydride 10 g (0.416 mole) and dry dimethyl formamide (500 ml). After 15 minutes, methyl iodide (59 g, 0.416 mole) was added dropwise at 15°–20° C. (external cooling) and the mixture stirred at room temperature for 2½ hours. Water was then added very cautiously until no further reaction occurred. Addition to a large excess of ice and filtration gave after drying 49 g (92%) buff solid which was shown to be the title product by NMR.

(b) 5-Bromo-2,3-dihydro-3,3-dimethylbenzofuran-2-one (II)

2-Methoxy-5-bromo-α,α-dimethylbenzyl cyanide (49 g, 0.193 mole) was heated under reflux in hydrobromic acid (400 ml, 48% aqueous) for about 20 hours. The reaction mixture was cooled and extracted with ether. The ether extracts were washed with water dried over magnesium sulphate and run down leaving a dark brown oil (39.2 g, 84%) which solidified on standing. The structure of the title product was confirmed by NMR and IR. A purified sample had m.p. 55°–6° C.

(c) 5-Cyano-2,3-dihydro-3,3-dimethylbenzofuran-2-one (I)

5-Bromo-2,3-dihydro-3,3-dimethylbenzofuran-2-one (39.2 g, 0.162 mole) was treated with cuprous cyanide (17.9 g, 0.2 mole) in dimethyl formamide (40 ml) (as in example 2). Recrystallisation (twice) of the product from ethanol yielded 14 g (45%) title product m.p. 138°–140° C.

$C_{10}H_9NO_2$ requires: C, 68.56; H, 5.18; N, 8.00. Found: C, 68.29; H, 4.91; N, 8.05%.

EXAMPLE 4

5-Bromo-2,3-dihydro-3,3-dimethylbenzofuran-2-one (II)—alternative route (a) 2-Methoxy-α,α-dimethylbenzylcyanide By a method analogous to that of Example 3(a), o-methoxybenzyl cyanide was methylated with methyl iodide and sodium hydride in dimethylformamide to give the desired compound in 85% yield.

(b) 2,3-Dihydro-3,3-dimethylbenzofuran-2-one

By a method analogous to that of Example 3(b), 2-methoxy-α,α-dimethylbenzylcyanide was cyclised to give the desired compound (80% yield) by means of 48% aqueous hydrobromic acid.

(c) 5-Bromo-2,3-dihydro-3,3-dimethylbenzofuran-2-one (II)

2,3-Dihydro-3,3-dimethylbenzofuran-2-one (1.62 g, 0.01 mole), in carbon tetrachloride (25 ml) containing catalytic amounts of iron filings and iodine was treated with bromine (1.6 g, 0.01 mole) and the mixture boiled under reflux for 1 hour. The solvent was removed under vacuum and the residue taken up in petroleum ether (b.p. 60°–80° C.). The solution was decanted from a little insoluble residue and washed with aqueous sodium metabisulphite and water, dried over magnesium sulphate and run down. The title product was obtained as a white solid m.p. 49°–53° C. and was shown by NMR to be a slightly impure sample of the product obtained in Example 3(b).

EXAMPLE 5

5-Cyano-2,3-dihydro-3,3-dimethyl-2-ethoxybenzofuran (I)

(a) 2-(2-Methoxy-5-bromophenyl)-2-methyl-1-chloropropane

β-Methallyl chloride (90.5 g, 1.0 mole) was added dropwise to a stirred mixture of p-bromoanisole (200 g, 1.07 mole) and sulphuric acid (34.2 g, 0.35 mole) at 35°–40° C. over about 2 hours. After 2½ hours at ambient temperature, the mixture was dissolved in dichloromethane, washed with water, aqueous sodium bicarbonate and water again, dried over magnesium sulphate and run down. Distillation of the residue gave a small forerun b.p. about 54° C. at 0.2 mm Hg and a main fraction of 182 g (62%) b.p. 99°–120° C. at 0.15–0.2 mm Hg. Recrystallisation from petroleum ether (b.p. 80°–100° C.) gave 137 g pure title product m.p. 82°–4° C. Reduction in volume of the mother liquors afforded a further 14 g product.

(b) 2-(2-Methoxy-5-bromophenyl)-2-methyl-1-propyl methylsulphide (IX)

Methyl mercaptan (34 g, 0.7 mole) was dissolved in dimethyl formamide (400 ml) and sodium methoxide (38 g, 0.7 mole) was added portionwise with ice cooling. The mixture was stirred for 10 minutes and 2-(2-methoxy-5-bromophenyl)-2-methyl-1-chloropropane (130 g, 0.47 mole) added all at once prior to heating to reflux. Boiling under reflux (118°–124° C.) was continued for 2 hours. Cooling, addition to ice-water and isolation through ether gave a crude yield of 126 g. This product was distilled yielding a forerun of 20 g b.p. 64°–84° C. at 0.3–0.1 mm and a main fraction of 97.4 g b.p. 98°–133° C. at 0.05 mm. The main fraction was shown by NMR to contain about 50% demethylated material (free hydroxyl).

This mixture was added to sodium hydroxide solution (200 ml, 20%) and dimethyl sulphate (38 g, 0.3 mole) was added dropwise with stirring at 22°–5° C. After 3 hours at room temperature, ammonium hydroxide solution (50 ml) was added and the product extracted into ether. Washing the extracts with water, drying over magnesium sulphate, running down and distilling yielded 79.3 g (58%) title sulphide b.p. 93°–8° C. at 0.02 mm.

(c) 2-(2-Methoxy-5-bromophenyl)-2-methyl-1-chloropropyl methyl sulphide (VIII)

N-Chlorosuccinimide (37.4 g, 0.28 mole) was added portionwise to 2-(2-methoxy-5-bromophenyl)-2-methyl-1-propyl methyl sulphide (79.3 g, 0.275 mole) in carbon tetrachloride (250 ml) at room temperature. An exothermic reaction ensued, the temperature being allowed to rise to 40° C. before control with an external cooling bath was applied. After addition, the reaction mixture was heated at about 40° C. for 4 hours, then cooled, filtered and run down yielding 88 g crude title product (99%).

(d) 2-(2-Methoxy-5-bromophenyl)-2-methyl-1-propanol 2-(2-Methoxy-5-bromophenyl)-2-methyl-1-chloropropyl methyl sulphide (67 g) in ethanol (100 ml) was added dropwise over 20 minutes to a refluxing mixture of ethanol (400 ml) and water (500 ml) with vigorous stirring. The mixture was stirred and refluxed for 1½ hours prior to removal of the ethanol by distillation. Cooling and isolation through ether yielded 54 g crude product. Distillation of this product gave a main fraction of 30.4 g b.p. 78°–95° C. at 0.05 mm which was shown by NMR to be slightly impure title aldehyde. The residue of 18 g was mainly the dithioacetal of the title aldehyde. This residue was dissolved in dichloromethane (80 ml) and silica gel (50 g) and water (5 ml) added. To this stirred mixture was then added dropwise with stirring, sulphuryl chloride (7.3 g, 0.054 mole) at 20°–5° C. Stirring was continued for 2 hours, after which time the silica gel was removed by filtration, the solution washed with dilute sodium hydroxide solution and water, dried and run down giving a yellow oil, 11.6 g which was proved to be title aldehyde by NMR. The total yield was 42 g (80%).

(e)
5-Bromo-2,3-dihydro-3,3-dimethyl-2-hydroxybenzofuran (II)

2-(2-Methoxy-5-bromophenyl)-2-methyl-1-propanal (30 g, 0.115 mole) was added to molten pyridine hydrochloride (60 g) and the mixture heated with stirring at 190°–200° C. for 50 minutes. Addition to ice-water containing a little hydrochloric acid and isolated through ether gave, after recrystallisation from petroleum ether (b.p. 80°–100° C.) 11.7 g (42%) title product m.p. 114°–5° C.

(f)
5-Bromo-2,3-dihydro-3,3-dimethyl-2-ethoxybenzofuran (II)

5-Bromo-2,3-dihydro-3,3-dimethyl-2-hydroxybenzofuran (5 g, 0.02 mole) was heated under reflux in ethanol (30 ml) with sulphuric acid (4 drops) for 1½ hour. The solution was cooled, neutralised with a few drops of triethylamine and run down. The residue was redissolved in ether and the solution washed with water, dried over magnesium sulphate and the solvent removed under vacuum leaving 4.7 g (86%) title product as a buff-coloured oil. The structure was confirmed by NMR.

(g)
5-Cyano-2,3-dihydro-3,3-dimethyl-2-ethoxybenzofuran (I)

5-Bromo-2,3-dihydro-3,3-dimethyl-2-ethoxybenzofuran (4.7 g, 0.017 mole) was heated under reflux with cuprous cyanide (2.7 g, 0.03 mole) in dimethyl formamide (10 ml) as in example 2 for 3 hours. A warm solution of sodium cyanide (5 g) in water (20 ml) was added with stirring and stirring was continued for 1 hour at ambient temperature. The solution was diluted with water and extracted with ether. The extracts were washed with water, dried over magnesium sulphate and run down yielding 3.6 g crude product. Purification was accomplished by silica gel chromatography in 1:4 ether/petroleum ether (b.p. 40°–60° C.). The yield of pure title product was 2.9 g (79%).

$C_{13}H_{15}NO_2$ requires: C, 71.86; H, 6.96; N, 6.45. Found: C, 71.64; H, 6.78; N, 6.68%.

EXAMPLE 6

5-Cyano-2,3-dihydro-3,3-dimethylbenzofuran (I)—alternative route (a) 5-Bromo-2,3-dihydro-3,3-dimethylbenzofuran (II)

2-(2-Methoxy-5-bromophenyl)-2-methyl-1-chloropropane (from example 5(a)) (120 g, 0.43 mole) was heated under reflux (163°–9° C.) with pyridine hydrochloride (220 g) in quinoline (220 g) with stirring for 3 hours. Addition to iced dilute hydrochloric acid and isolation through ether gave after distillation 73 g (75%) title product b.p. 62°–4° C. at 0.01 mm Hg.

(a') 5-Bromo-2,3-dihydro-3,3-dimethylbenzofuran (II)—alternative route

β-Methallyl chloride (45.2 g, 0.5 mole) was added dropwise over about 30 minutes to a slurry of p-bromophenol and sulphuric acid at 33°–7° C. Stirring was continued at 25°–30° C. for 20 minutes prior to dissolution in ether. The ethereal solution was washed with water, dried and run down. The residue was immediately added to 300 ml 20% aqueous sodium hydroxide and the mixture stirred at room temperature for 17 hours. Ether extraction and work-up yielded, after distillation, 33 g crude title product (29%) b.p. 70°–102° C. at 0.3–0.1 mm Hg.

(b) 5-Cyano-2,3-dihydro-3,3-dimethylbenzofuran (I)

5-Bromo-2,3-dihydro-3,3-dimethylbenzofuran (15 g, 0.066 mole) was heated under reflux with cuprous cyanide (7.2 g. 0.08 mole) in dimethyl formamide (15 ml) as in Example 2. Work up yielded, after recrystallisation from petroleum ether (bp 60°–80° C.) with charcoaling, 5.7 g of product, mp 72°–75° C.

EXAMPLE 7

5-Cyano-2,3-dihydro-3,3-dimethyl-2-methoxybenzofuran (I)

By a method analogous to that of Example 5, the above compound was prepared in 65% yield, mp 61°–62° C.

Analysis: $C_{12}H_{13}NO_2$ requires: C, 70.91; H, 6.45; N, 6.89%. Found: C, 70.50; H, 6.20; N, 6.71%.

EXAMPLE 8

5-Cyano-2,3-dihydro-3,3-dimethyl-2-(2'-methylpropoxy)benzofuran (I)

By a method analogous to that of Example 5, the above compound was prepared in 83% yield, mp 54°–56° C.

Analysis: $C_{15}H_{19}NO_2$ requires: C, 73.44; H, 7.81; N, 5.71%. Found: C, 73.06; H, 7.88; N, 5.40%.

EXAMPLE 9

5-Cyano-2,3-dihydro-3,3-dimethyl-2-acetoxybenzofuran (I)

(a)
5-Bromo-2,3-dihydro-3,3-dimethyl-2-acetoxybenzofuran (II)

Acetyl chloride (2.0 g) in diethyl ether (10 ml) was added dropwise to a stirred, cooled solution of 5-bromo-2,3-dihydro-3,3-dimethyl-2-hydroxybenzofuran (5.0 g), prepared as in Example 5(e), and triethylamine (2.5 g) in diethyl ether (40 ml). After stirring for 3 hours at room temperature the mixture was washed with water three times, dried over magnesium sulphate and run down to yield 5 g of crude product, mp 73°-80° C., which was recrystallised from petroleum ether (80°-100° C.) with charcoaling to give 4 g of pure product, mp 83°-85° C.

(b)
5-Cyano-2,3-dihydro-3,3-dimethyl-2-acetoxybenzofuran (I)

The product from stage (a) (4 g), cuprous cyanide (1.8 g) and dimethylformamide (10 ml) were boiled under reflux with stirring for three hours. The mixture was then cooled, and a solution of sodium cyanide (4.5 g) in water (18 ml) was added. After stirring for 1 hour, the product was extracted into ether, the ethereal extract being washed with water (twice), dried over magnesium sulphate, and run down. Recrystallisation of the residue from ethanol gave 1.8 g of pure product, mp 140°-142° C.

Analysis: Found: C, 67.09; H, 6.00; N, 6.18%. $C_{13}H_{13}NO_3$ requires: C, 67.52; H, 5.67; N, 6.06%.

EXAMPLE 10

5-Cyano-2,3-dihydro-3,3-dimethyl-2-hydroxybenzofuran (I)

5-Bromo-2,3-dihydro-3,3-dimethyl-2-hydroxybenzofuran (7.3 g), prepared as in Example 5(e) and cuprous cyanide (3.2 g) were heated under reflux in dimethylformamide (10 ml) with stirring for 5½ hours. The mixture was cooled to room temperature and a solution of ferric chloride (6 g) in water (20 ml) containing hydrochloric acid (3.7 ml conc) was added. After heating at 60°-70° C. for 20 minutes the mixture was extracted with ether. The extracts were washed with water (twice), dried over magnesium sulphate and run down under vacuum to give 4.6 g of product, which on recrystallisation from toluene gave 2.0 g pure title product, mp 124°-127° C.

Analysis: Found: C, 70.09; H, 6.04; N, 7.24%. $C_{11}H_{11}NO_2$ requires: C, 69.82; H, 5.86; N, 7.40%.

EXAMPLE 11

5-Cyano-2,3-dihydro-3,3-dimethyl-2-isopropoxybenzofuran (I)

By a method analogous to that of Example 5(f), but stating with the product of Example 10, the above compound was prepared in 80% yield as a pale yellow oil.

Analysis: Found: C, 72.73; H, 7.80; N, 5.91%. $C_{14}H_{17}NO_2$ requires: C, 72.70; H, 7.41; N, 6.06%.

EXAMPLE 12

5-Cyano-2,3-dihydro-3,3-dimethyl-2-n-propoxybenzofuran (I)

By a method analogous to that of Example 5(f), but starting with the product of Example 10, the above compound was prepared in 79% yield as a pale yellow oil.

Analysis Found: C, 72.20; H, 7.69; N, 6.01%. $C_{14}H_{17}NO_2$ requires: C, 72.70; H, 7.41; N, 6.06%.

EXAMPLE 13

5-Cyano-2,3-dihydro-3,3-dimethylbenzofuran-2-yl N-methylcarbamate (I)

Methyl isocyanate (1.75 g) was added to 2,3-dihydro-3,3-dimethyl-2-hydroxybenzofuran (5 g), prepared as in Example 10, in diethyl ether (50 ml), followed by triethylamine (4 drops) as catalyst. The mixture was left overnight and was then filtered, giving 2 g of crude title product. Recrystallisation from methanol gave 1.3 g of pure product, mp 177° C.

Analysis: $C_{13}H_{14}N_2O_3$ requires: C, 63.40; H, 5.73; N, 11.38%. Found: C, 63.86; H, 5.77; N, 11.53%.

EXAMPLE 14

5-Cyano-2,3-dihydro-3,3-dimethylbenzofuran-2-yl N-phenylcarbamate (I)

By a method analogous to that of Example 13 the above compound was prepared in 89% yield, mp 136° C.

Analysis: $C_{18}H_{16}N_2O_3$ requires: C, 70.11; H, 5.23; N, 9.09%. Found: C, 69.70; H, 5.10; N, 9.13%.

EXAMPLE 15

2-Chloro-5-cyano-2,3-dihydro-3,3-dimethylbenzofuran (I)

Thionyl chloride (9.3 g) in dichloromethane (10 ml) was added dropwise with stirring and cooling to 5-cyano-2,3-dihydro-3,3-dimethyl-2-hydroxybenzofuran (11.3 g) prepared as in Example 10 and pyridine (6.2 g) in dichloromethane (60 ml). The mixture was stirred for 2 hours at room temperature prior to washing with water, dilute sodium hydroxide solution and water again, drying over magnesium sulphate and evaporating under vacuum. Recrystallisation from toluene and petroleum ether (bp 80°-100° C.) gave 9.7 g of the title compound, mp 105°-106° C.

Analysis: $C_{11}H_{12}ClNO$ requires: C, 63.01; H, 5.77; N, 6.68%. Found: C, 62.55; H, 5.34; N, 6.58%.

EXAMPLE 16

5-Cyano-2,3-dihydro-3,3-dimethyl-2-isothiocyanatobenzofuran (I)

2-Chloro-5-cyano-2,3-dihydro-3,3-dimethylbenzofuran (5 g) from Example 15 and potassium thiocyanate (4.6 g) were heated in dimethylformamide (30 ml) at 110° C. for 7 hours. The mixture, after cooling, was added to water and the product extracted into diethyl ether. The ether solution was washed with water (twice), dried over magnesium sulphate and run down under vacuum yielding 4 g of crude product. Purification by silica gel chromatography in toluene yielded 1.2 g of title product, mp 52° C.

Analysis: $C_{12}H_{10}N_2OS$ requires: C, 62.59; H, 4.38; N, 12.17%. Found: C, 62.14; H, 4.44; N, 11.75%.

EXAMPLE 17

2-Chloroacetoxy-5-cyano-2,3-dihydro-3,3-dimethylbenzofuran (I)

Chloroacetyl chloride (3.6 g) was added dropwise to a solution of 5-cyano-2,3-dihydro-3,3-dimethyl-2-hydroxybenzofuran (5 g) prepared as in Example 10, and triethylamine (3.2 g) in diethyl ether (50 ml) with stirring and cooling. After 3 hours at room temperature, the mixture was shaken with water and an insoluble solid product was filtered off and dried to give 2.4 g of title compound, mp 138° C.

Analysis: $C_{13}H_{12}ClNO_3$ requires: C, 58.76; H, 4.55; N, 5.27%. Found: C, 59.08; H, 5.03; N, 5.42%.

In the same reaction, 2-(5-cyano-2-chloroacetoxyphenyl)-2-methyl-1-propanal was also produced.

EXAMPLE 18

2-n-Butyryloxy-5-cyano-2,3-dihydro-3,3-dimethylbenzofuran (I)

By a method analogous to that of Example 17 the above compound was prepared in 20% yield, mp 78° C.

Analysis: $C_{15}H_{17}NO_3$ requires: C, 69.48; H, 6.61; N, 5.40%. Found: C, 69.75; H, 6.98; N, 5.53%.

In the same reaction 2-(5-cyano-2-n-butyryloxyphenyl)-2-methyl-1-propanal was also produced.

EXAMPLE 19

5-Cyano-2,3-dihydro-3,3-dimethyl-2-isovaleroyloxybenzofuran (I)

By a method analogous to that of Example 17 the above compound was prepared in a 17% yield, mp 83°–84° C.

Analysis: $C_{16}H_{19}NO_3$ requires: C, 70.31; H, 7.01; N, 5.13%. Found: C, 70.66; H, 7.09; N, 5.05%.

In the same reaction 2-(5-cyano-2-isovaleroyloxyphenyl)-2-methyl-1-propanal was also produced.

EXAMPLE 20

5-Cyano-2,3-dihydro-3,3-dimethyl-2-isobutyryloxybenzofuran (I)

By a method analogous to that of Example 17 the above compound was prepared in a 65% yield, mp 128° C.

Analysis: $C_{15}H_{17}NO_3$ requires: C, 69.48; H, 6.61; N, 5.40%. Found: C, 69.00; H, 6.67; N, 5.32%.

In the same reaction 2-(2-isobutyryloxy-5-cyanophenyl)-2-methyl-1-propanal was also produced.

EXAMPLE 21

5-Cyano-2,3-dihydro-3,3-dimethyl-2-n-valeroyloxybenzofuran (I) and 2-(5-cyano-2-n-valeroyloxyphenyl)-2-methyl-1-propanal (III)

By a method analogous to that of Example 17 the above compounds were prepared and separated by chromatography on silica gel, eluting with diethyl ether/petroleum ether bp 60°–80° C. (1:4), to give the benzofuran in 8% yield, mp 48°–52° C. and the propanal in 6% yield, mp 42° C.

Analysis: $C_{16}H_{19}NO_3$ requires: C, 70.31; H, 7.01; N, 5.13%. Found (benzofuran isomer): C, 69.83; H, 7.44; N, 4.97%. Found (propanal isomer): C, 70.01; H, 6.59; N, 5.37%.

EXAMPLE 22

2-(5-Cyano-2-propionyloxyphenyl)-2-methyl-1-propanal (III)

Propionyl chloride (3.0 g) was added dropwise with stirring and cooling to a solution of 5-cyano-2,3-dihydro-3,3-dimethyl-2-hydroxybenzofuran (5 g) prepared as in Example 10 and triethylamine (3.2 g) in diethyl ether (50 ml). After three hours stirring at room temperature, the mixture was washed twice with water, dried over magnesium sulphate and run down under vacuum to give 5.9 g of crude product containing about 20% by weight of 5-cyano-2,3-dihydro-3,3-dimethyl-2-propionyloxybenzofuran (I). Recrystallisation first from petroleum ether bp 80°–100° C. then from isopropanol gave 1.6 g of the desired propanal, mp 73° C.

Analysis: $C_{14}H_{15}NO_3$ requires: C, 68.55; H, 6.16; N, 5.71%. Found: C, 69.00; H, 5.99; N, 5.78%.

EXAMPLE 23

2-(2-Acryloyloxy-5-cyanophenyl)-2-methyl-1-propanal (III)

By a method analogous to that of Example 22 the above compound was prepared in 8% yield, mp 98° C.

Analysis: $C_{14}H_{13}NO_3$ requires: C, 69.12; H, 5.39; N, 5.76%. Found: C, 68.70; N, 5.60; N, 6.05%.

In the same reaction 5-cyano-2,3-dihydro-3,3-dimethyl-2-acryloyloxybenzofuran (I) was also produced.

EXAMPLE 24

2-(2-Methoxy-5-cyanophenyl)-2-methyl-1-propanal (III)

2-(2-Methoxy-5-bromophenyl)-2-methyl-1-propanal (9.5 g), prepared as in Example 5(d), cuprous cyanide (4.0 g) and dimethylformamide (20 ml) were heated under reflux with stirring for 3 hours. A solution of ferric chloride (7.3 g) in water (25 ml) and hydrochloric acid (3.5 ml conc) was added to the cooled reaction mixture which was then heated at 60°–70° C. for 5 minutes. Isolation of the product through diethyl ether yielded, after recrystallisation from ethanol, 3 g of pure product, mp 115°–117° C.

Analysis: Found: C, 71.05; H, 6.48; N, 6.41%. $C_{12}H_{13}NO_2$ requires: C, 70.91; H, 6.45; N, 6.89%.

EXAMPLE 25

2-(2-Methoxy-5-cyanophenyl)-2-methyl-1-propanal (III) alternative route 2-(2-Methoxy-5-bromophenyl)-2-methyl-1-chloropropylmethyl sulphide (10 g) prepared as in Example 5(c), in dichloromethane (10 ml) was added dropwise to silica gel (20 g) and water (2 ml) in dichloromethane (40 ml) at 20°–25° C. After stirring for 15 minutes at ambient temperature the mixture was treated dropwise with sulphuryl chloride (2.4 g) in dichloromethane (10 ml) at 20°–25° C. and stirring was continued for a further 2 hours. Filtration, washing the solution with water, aqueous sodium hydroxide and then with water again, followed by drying over magnesium sulphate and running down gave 6 g of crude product.

EXAMPLE 26

2-(2-Hydroxy-5-cyanophenyl)-2-propanol

5-Cyano-2,3-dihdyro-3,3-dimethyl-2-hydroxybenzofuran (2.0 g), prepared as in Example 10, was dissolved in methanol (10 ml) and added to sodium hydroxide (1.7 g) in water (25 ml) at 10°–15° C. with stirring. To this solution was added sodium borohydride (0.5 g), and the mixture was stirred at ambient temperature for 1½ hours. After acidification with hydrochloric acid (6 ml) at 8°–12° C., the mixture was filtered and the product washed with water and dried yielding 1.8 g. Recrystallisation from toluene gave 1.2 g of product, mp 129°–130° C.

Analysis: Found: C, 68.84; N, 7.10; N, 7.29%. $C_{11}H_{13}NO_2$ requires: C, 69.09; H, 6.85; N, 7.33%.

EXAMPLE 27

2-(5-Cyano-2-propionyloxyphenyl)-2-methyl-1-propyl propionate

Propionyl chloride (5.1 g) was added dropwise to 2-(2-hydroxy-5-cyanophenyl)-2-methyl-1-propanol (5 g) prepared as in Example 26 and triethylamine (5.5 g) in diethyl ether (50 ml) with stirring and cooling. After stirring for 3 hours at room temperature, the mixture was washed twice with water, dried over magnesium sulphate and run down, giving 6.5 g of crude product. After filtration through alumina in toluene, 5.3 g of title product were obtained as a viscous oil.

Analysis: $C_{17}H_{21}NO_4$ requires: C, 67.31; H, 6.98; N, 4.62%. Found: C, 66.82; H, 7.30; N, 4.51%.

EXAMPLE 28

2-(2-Chloroacetoxy-5-cyanophenyl)-2-methyl-1-propyl chloroacetate

By a method analogous to that of Example 27, the above compound was prepared in 30% yield, mp 64°–66° C.

Analysis: $C_{15}H_{15}Cl_2NO_4$ requires: C, 52.34; H, 4.39; N, 4.07%. Found: C, 52.31; H, 3.98; N, 4.05%.

EXAMPLE 29

2-(2-Isobutyryloxy-5-cyanophenyl)-2-methyl-1-propyl isobutyrate

By a method analogous to that of Example 27, the above compound was prepared in 33% yield, mp 71°–73° C.

Analysis: $C_{19}H_{25}NO_4$ requires: C, 68.86 H, 7.60 N, 4.23%. Found: C, 68.71 H, 8.02 H, 4.29%.

EXAMPLE 30

2-(2-Acetoxy-5-cyanophenyl)-2-methyl-1-propyl acetate

Acetyl chloride (3.5 g) in diethyl ether (10 ml) was added portionwise with swirling and ice cooling (5°–10° C.) to 2-(5-cyano-2-hydroxyphenyl)-2-methyl-1-propanol (3.8 g) prepared as in Example 26 and triethylamine (4.6 g) in diethyl ether (40 ml). The mixture was allowed to warm to room temperature, and was left for three hours before washing with water twice, drying over magnesium sulphate, and running down. The crude product (4 g) was dissolved in toluene and filtered through a bed of aluminium oxide. Removal of the toluene left the title product (2.3 g) as a colourless oil.

Analysis: $C_{15}H_{19}NO_4$ requires: C, 65.44; H, 6.22; N, 5.09%. Found: C, 64.98; H, 6.37; N, 4.77%.

EXAMPLE 31

2-(2-Hydroxy-5-cyanophenyl)-2-methyl N,N-dimethyl-propanoamide

A suspension of 5-cyano-2,3-dihydro-3,3-dimethylbenzofuran-2-one (3.7 g), prepared as in Example 3, in diethyl ether (50 ml) was treated with a solution of dimethylamine in ethanol (8.6 ml of a 20.8% solution) portionwise with stirring at room temperature. The mixture was stirred for two hours, and the product was isolated by filtration, yield 4 g, mp 146°–148° C.

Analysis: Found: C, 67.53; H, 7.40; N, 11.64%. $C_{13}H_{16}N_2O_2$ requires C, 67.22; H, 6.94; N, 12.06%.

EXAMPLE 32

2-(2-Hydroxy-5-cyanophenyl)-2-methyl methyl propanoate

Sodium methoxide (1.2 g) in methanol (15 ml) was added dropwise to a stirred suspension of 5-cyano-2,3-dihydro-3,3-dimethylbenzofuran-2-one (3.7 g), prepared as in Example 3, in methanol (30 ml) at 8°–10° C. After 2 hours stirring at room temperature, the reaction mixture was poured onto ice, filtered, and the solution was acidified with hydrochloric acid. Diethyl ether extraction, washing with water, drying over magnesium sulphate and running down gave crude product which, after recrystallisation from toluene yielded 3.1 g of product, mp 118°–122° C.

Analysis: Found: C, 66.01; H, 6.47; N, 6.54%. $C_{12}H_{13}NO_3$ requires: C, 65.74; H, 5.98; N, 6.39%.

EXAMPLE 33

7-Cyano-4,5-dihydro-2,2,5,5-tetramethyl-1,3-benzodioxepin

A suspension of 2-(5-cyano-2-hydroxyphenyl)-2-methyl-1-propanol (5 g), prepared as in Example 26, in 2,2-dimethoxypropane was treated with 2 drops sulphuric acid at 10° C. After 1 hour at ambient temperature, diethyl ether was added, and the solution was washed with sodium hydroxide solution and water (twice). It was then dried over magnesium sulphate and run down, yielding 2.4 g of an oil which solidified on standing. The solid was dissolved in petroleum ether (bp 40°–60° C.) and the solution was cooled in an ice/salt bath. The resulting crystalline solid was separated off by filtration, yielding 1.9 g of product, mp 55°–56° C.

Analysis: $C_{14}H_{17}NO_2$ requires: C, 72.70; H, 7.41; N, 6.06%. Found C, 72.30; H, 7.73; N, 6.10%.

EXAMPLE 34

7-Cyano-4,5-dihydro-5,5-dimethyl-1,3,2-benzodioxathiepin 2-oxide

Thionyl chloride (4.2 g) in diethyl ether (10 ml) was added dropwise with stirring at 0°–5° C. to a solution of 2-(5-cyano-2-hydroxyphenyl)-2-methyl-1-propanol (5 g) prepared as in Example 26, and pyridine (5.5 g) in diethyl ether (80 ml). The mixture was stirred for 3 hours at 0°–20° C. Water was then added and the mixture was filtered. The ether solution was then washed with dilute hydrochloric acid, when with aqueous sodium bicarbonate and water (twice), then dried over magnesium sulphate and run down. The residue was recrystallised from ethanol, giving the title product (2.0 g) as white crystals, mp 87°–88° C.

Analysis: $C_{11}H_{11}NO_3S$ requires: C, 55.68; H, 4.67; N, 5.90%. Found: C, 55.20; H, 4.60; N, 5.75%.

EXAMPLE 35

2,3-Dihydro-3,3-dimethyl-5-cyanobenzofuran (I)

The procedure of Example 6(a') was followed employing p-chlorophenol instead of the p-bromophenol as starting material. 5-Chloro-2,3-dihydro-3,3-dimethylbenzofuran was obtained in 38% yield, bp 45°–53° C. at 0.1 mm Hg. By the procedure of Example 6(b) this was converted into 8.4 g of 2,3-dihydro-3,3-dimethyl-5-cyanobenzofuran, mp 64°–66° C.

EXAMPLE 36

2,3-Dihydro-3,3-dimethyl-5-cyanobenzofuran (I)

(a) 2,3-Dihydro-3,3-dimethylbenzofuran-5-carboxylic acid 2,3-Dihydro-3,3-dimethyl-5-bromobenzofuran (30 g) prepared as in Example 6(a) was reacted with magnesium (3.4 g) in dry diethyl ether. Carbon dioxide as bubbled through this solution for 2 hours prior to standing overnight and decomposition of the complex by addition of dilute hydrochloric acid at 10°–15° C. The diethyl ether was separated and the product was extracted into dilute aqueous sodium hydroxide. Acidification, extraction into diethyl ether and recrystallisation from petroleum ether (bp 60°–80° C.) gave 7.9 g of title product, mp 171°–173° C.

Analysis: $C_{11}H_{12}O_3$ requires: C, 68.73; H, 6.29%. Found: C, 68.55; H, 5.92%.

(b) 2,3-Dihydro-3,3-dimethylbenzofuran-5-carboxylic acid chloride

The product of stage (a) (3 g) was boiled under reflux in thionyl chloride (3.6 g) for 3 hours. Removal of the thionyl chloride under vacuum gave crude title product (4.2 g).

(c) 2,3-Dihydro-3,3-dimethylbenzofuran-5-carboxylic acid amide (II)

The product of stage (b) (4.2 g) was added dropwise to excess aqueous ammonia with stirring and ice cooling. After 1 hour the white precipitate was filtered off and recrystallised from ethanol to give 1.1 g of title product, mp 136°–138° C.

Analysis: $C_{11}H_{13}NO_2$ requires: C, 69.09; H, 6.85; N, 7.33%. Found: C, 69.43; H, 7.22; N, 7.36%.

(d) 2,3-Dihydro-3,3-dimethyl-5-cyanobenzofuran (I)

The product of stage (c) was boiled under reflux in benzene (5 ml) with thionyl chloride for 6 hours. Washing with water, drying over magnesium sulphate and running down gave, after recrystallisation from petroleum ether (bp 60°–80° C.), 0.6 g of title product, mp 70°–72° C.

EXAMPLE 37

5-Cyanospiro[benzofuran-3(2H)-1'-cyclohexan]-2-one (I)

By a method analogous to that of Example 2 but starting with 1-cyano-1-(2-methoxy-5-bromophenyl)cyclohexane (prepared by reaction of 2-methoxy-5-bromobenzyl cyanide and sodium hydride, followed by reaction with 1,5-pentamethylenedibromide) the above compound was prepared, mp 172°–174° C.

Analysis: $C_{14}H_{13}NO_2$ requires: C, 74.0; H, 5.8; N, 6.2%. Found: C, 73.6; H, 6.0; N, 5.9%.

EXAMPLE 38

5-Cyano-2,3-dihydro-3-methyl-3-isopropylbenzofuran-2-one (I)

(a) 2-Methoxy-5-chloro-α-isopropylbenzyl cyanide

To a stirred suspension of sodium hydride (2.4 g) in dimethylformamide (100 ml) was added a solution of 2-bromopropane and 2-methoxy-5-chlorobenzyl cyanide (18.2 g) in dry dimethylformamide (50 ml), keeping the temperature at 20°–30° C. The mixture was then stirred for 30 minutes, water was added cautiously, and the mixture was then poured into ice-water. Hydrochloric acid was then added and the mixture was extracted with dichloromethane, washed with water then with sodium chloride solution, then dried over magnesium sulphate, filtered, and the solvent was then removed to give 25 g of a brown oil. Distillation gave the title product (15 g) as a colourless oil, bp 180° C./20 mm Hg.

(b) 2-Methoxy-5-chloro-αmethyl-α-isopylbenzyl cyanide

To a stirred suspension of sodium hydride (2.0 g) in dry dimethylformamide (100 ml) was added a solution of methyl iodide (12.4 g) and the product of stage (a) in dry dimethylformamide (50 ml), keeping the temperature at 20°–30° C. The reaction mixture was stirred for 30 minutes, water was added cautiously, and the mixture was then poured into ice water. Hydrochloric acid was added and the product was extracted with dichloromethane, washed with water then with brine, then dried over magnesium sulphate and filtered, the solvent being removed to give a brown oil which slowly crystallised. Recrystallisation from petroleum ether gave the title product as colourless needles, mp 94°–95° C.

(c) 5-Chloro-2,3-dihydro-3-methyl-3-isopropylbenzofuran-2-one (I)

By a method analogous to that of Example 3 stage (b) the above compound was prepared as colourless needles, mp 28°–29° C.

Analysis: $C_{12}H_{13}ClO_2$ requires: C, 64.1; H, 5.8%. found: C, 64.7; H, 5.5%.

(d) 5-Cyano-2,3 dihydro-3-methyl-3-isopropylbenzofuran-2-one (I)

By a method analogous to that of Example 3 stage (c) the above compound was prepared as colourless needles, mp 117°–118° C.

Analysis: $C_{13}H_{13}NO_2$ requires: C, 72.5; H, 6.1; N, 6.5%. found: C, 72.2; H, 5.8; N, 6.8%.

EXAMPLE 39

5,7-Dicyanospiro[benzofuran-3(2H)-1'-cyclohexan]-2-one (I)

(a) 2,4-Dibromo-6-methylphenol

To a stirred solution of 2-methylphenol (108 g) in tetrachloromethane (400 ml) bromine (320 g) was added dropwise. The reaction mixture was stirred for 15 minutes and the solvent was evaporated off to give the title product as an oil (266 g).

(b) 2,4-Dibromo-6-methylanisole

To a stirred solution of the product of stage (a) (266 g) in 4 N aqueous sodium hydroxide (900 ml), dimethyl sulphate (192 ml) was added whilst maintaining the temperature at 35°–40° C. The mixture was stirred for 5 minutes, then 4 N aqueous sodium hydroxide (450 ml) was added and dimethyl sulphate (96 ml) was added dropwise. The temperature rose to 55° C. The mixture was then stirred overnight, and the product was extracted into dichloromethane, washed with water, dried over magnesium sulphate, filtered, and the solvent evaporated off to give a brown oil (280 g). Distillation gave the title product as a colourless oil, bp 96°–98° C./0.3 mm Hg.

(c) 2,4-Dibromo-6-bromomethylanisole

A solution of the product of stage (b) (200 g) and benzyl peroxide (1 g) in tetrachloromethane (600 ml) was heated to reflux with stirring. Bromine (114 g) was added dropwise, and the mixture was stirred until it cooled to room temperature. Evaporation of the solvent gave an oil, distillation of which gave the title compound (183 g) as an oil, bp 115°–116° C./0.3 mm Hg.

(d) 2,4-Dibromo-6-cyanomethylanisole

A solution of the product of stage (c) (183 g) in ethanol (150 ml) was heated to reflux. A solution of sodium cyanide (25 g) in hot water (50 ml) was added which maintained gentle refluxing. The mixture was then stirred for 5 minutes, poured into ice water, and the product was filtered off, taken up in dichloromethane, washed with water, dried over magnesium sulphate and filtered. The solvent was removed to give a brown oil which slowly crystallised. Recrystallisation from petroleum ether gave the title product as colourless needles, mp 87°–88° C.

(e) 1-Cyano-1-(2-methoxy-3,5-dibromophenyl)cyclohexane

To a stirred suspension of sodium hydride (7 g) in dry dimethylformamide (200 ml) was added a solution of 1,5-dibromopentane (20 ml) and the product of stage (d) in dimethylformamide (40 ml), keeping the temperature at 20°–30° C. The mixture was stirred for 30 minutes, water was added cautiously, and was then poured into ice water. Hydrochloric acid was added and the mixture was extracted with dichloromethane, washed with water and brine, dried over magnesium sulphate and filtered, and the solvent was removed to give a pale brown oil which slowly crystallised. Recrystallisation from ethanol gave the title product as yellow crystalls, mp 100°–102° C.

(f) 5,7-Dicyanospiro[benzofuran-3(2H)-1'-cyclohexan]-2-one (I)

By a method analogous to that of Example 2 but starting with the product of stage (e), the above compound was prepared (mp 169°–170° C.) via the corresponding 5,7-dibromospirobenzofuranone (mp 140°–141° C.)

Analysis: (dibromo compound) $C_{13}H_{12}Br_2O_2$ requires: C, 43.4; H, 3.4%. Found: C, 43.0; H, 3.5%.

Analysis: (dicyano compound) $C_{15}H_{12}N_2O_2$ requires: C, 71.4; H, 4.8; N, 11.1%. Found: C, 71.7; H, 5.2; N, 10.7%.

EXAMPLE 40

1-(2-Hydroxy-5-cyanophenyl)cyclopentane carboxylic acid

To a suspension of the compound of Example 2 (3.5 g) in ethanol (150 ml) was added a solution of sodium carbonate (3.5 g) in water (150 ml), and the mixture was stirred overnight. It was then poured into water and extracted with diethyl ether. The aqueous layer was made just acidic and was extracted with ethyl acetate, washed with water, then with brine, and was then dried over magnesium sulphate. Evaporation of the solvent gave the title product as colourless crystals, mp 153°–154° C. (2.0 g).

Analysis: $C_{13}H_{13}NO_3$ requires: C, 67.5; H, 5.7; N, 6.1. Found: C, 68.0; H, 5.2; N, 6.1.

EXAMPLE 41

1-(2-Hydroxy-5-cyanophenyl)-1-dimethylcarbamoylcyclopentane

To a suspension of the product of Example 2 (4.3 g) in diethyl ether (50 ml) with stirring was added a 20.8% solution of dimethylamine in ethanol (8.6 ml) at room temperature. The solid slowly dissolved to give a solution which precipitated the product, which was filtered off, washed with ethanol, taken up in chloroform, washed and dried. The solvent was removed to give the title product as a white powder, mp 144°–146° C. (2.3 g).

Analysis: $C_{15}H_{18}N_2O_2$ requires: C, 69.8; H, 7.0; N, 10.9%. Found: C, 68.4; H, 6.9; N, 11.0%.

EXAMPLE 42

1-(2-Hydroxy-5-cyanophenyl)-1-methoxycarbonylcyclopentane

To a stirred suspension of the product of Example 2 (4.3 g) in methanol (30 ml) at 8°–10° C. was added dropwise a solution of sodium methoxide (1.2 g) in methanol (15 ml). The solid rapidly dissolved and the resulting solution was stirred for 2 hours at room temperature, poured into water and filtered. The filtrate was acidified and the product was extracted into diethyl ether, washed with water, dried over magnesium sulphate and filtered. The solvent was evaporated off to give a colourless crystalline product which was recrystallised from toluene to give 2.3 g of the title product, mp 113°–118° C.

Analysis: $C_{14}H_{15}NO_3$ requires: C, 68.6; H, 6.2; N, 5.7%. Found: C, 68.3; H, 6.1; N, 5.2%.

EXAMPLE 43

5-Cyano-2,3-dihydro-3,3-dimethyl-2-ethoxybenzofuran (I)—alternative route

(a) 2-(2-Methoxy-5-cyanophenyl)-2-methyl-1-propanal (III)

A mixture of 2-(2-methoxy-5-bromophenyl)-2-methyl-1-propanal (97 g), produced as in Example 5(d), cuprous cyanide (47.5 g) and dimethylformamide (200 ml) was boiled under reflux with stirring for 3 hours. After cooling to room temperature the reaction mixture was treated with a solution of ferric chloride (86 g) in water (200 ml) and hydrochloric acid (53 ml concentrated). The mixture was kept at 30° C. by external cooling. Stirring was continued for 20 minutes at ambient temperature prior to extraction of the mixture with dichloromethane. The extract was washed with water (3 times), dried over magnesium sulphate, boiled with charcoal, filtered and run down to give 74 g of crude title product. Recrystallisation from ethanol yielded 57.6 g of pure product, mp 113°–115° C.

(b) 5-Cyano-2,3-dihydro-3,3-dimethyl-2-hydroxybenzofuran (I)

The product of stage (a) (57.6 g) was dissolved in quinoline (120 ml) and the solution was added to pyridine hydrochloride (120 g). The mixture was then stirred and refluxed for 4 hours. Addition to dilute iced hydrochloric acid, diethyl ether extraction, washing with dilute hydrochloric acid and water (twice), drying over magnesium sulphate and running down gave 53.6 g of crude title product, mp 103°–122° C. Recrystallisation from toluene yielded 36.3 g of pure title product, mp 127°–129° C.

(c) 2,3-Dihydro-3,3-dimethyl-5-cyano-2-ethoxybenzofuran (I)

The product of stage (b) (32.2 g) was boiled under reflux in ethanol (200 ml) containing sulphuric acid (7 drops), for 2 hours. The solution was cooled, neutralised with triethylamine and reduced to half volume under vacuum. Addition to water and isolation through diethyl ether gave 34.4 g of crude title product as a yellow oil. This was dissolved in petroleum ether bp 40°-60° C. containing 5% diethyl ether, then filtered through a bed of aluminium oxide followed by elution with the same solvent mixture. This yielded 30.5 g of the pure product as a colourless oil.

EXAMPLE 44

5-Cyano-2,3-dihydro-3,3-dimethyl-2-ethoxybenzofuran—alternative route (a) 2,5-Dichloro-2,3-dihydro-3,3-dimethylbenzofuran Chlorine was bubbled through a refluxing solution of 5-chloro-2,3-dihydro-3,3-dimethylbenzofuran (50 g) (prepared as in Example 6(a') employing p-chlorophenol instead of p-bromophenol as the starting material) and 2,2'-azobisisobutyronitrile (1.5 g) in carbon tetrachloride (200 ml) for 4½ hours. The reaction was monitored by nmr spectroscopy until monochlorination was complete. The solution was cooled, washed with aqueous sodium bicarbonate and water, dried over sodium sulphate, and run down under vacuum to give 59 g of crude product.

(b) 5-Chloro-2,3-dihydro-3,3-dimethyl-2-ethoxybenzofuran (II)

The product of stage (a) (25 g) was refluxed in ethanol (150 ml) for 2 hours. The ethanol was then removed under vacuum and the residue was redissolved in diethyl ether. Washing with water (twice), drying over sodium sulphate and running down gave, after distillation, 15.5 g of the desired product, bp 68°-72° C. at 0.2 mm Hg.

(c) 5-Cyano-2,3-dihydro-3,3-dimethyl-2-ethoxybenzofuran (I)

By the procedure of Example 6(b), the product of stage (b) was converted into the above compound (9.5 g), the structure of which was confirmed by nmr spectroscopy.

EXAMPLE 45

2-Chloro-5-cyano-2,3-dihydro-3,3-dimethylbenzofuran (I)—alternative route

By the method of Example 44, stage (a), the above compound (mp 105°-106° C.) was prepared from 5-cyano-2,3-dihydro-3,3-dimethylbenzofuran (17.3 g) prepared as in Example 1.

EXAMPLE 46

5-Cyano-2,3-dihydro-3,3-dimethyl-2-ethoxybenzofuran (I)—alternative route

By the method of Example 44(b), the above compound was prepared from the product of Example 45, its structure being confirmed by nmr spectroscopy.

EXAMPLE 47

5-Cyano-2,3-dihydro-3,3-dimethyl-2-hydroxybenzofuran (I)—alternative route

The product of Example 45 (2 g) was boiled under reflux in water (5 ml) and acetone (15 ml) for 3½ hours. The product was then extracted into diethyl ether, the extracted solution then being washed twice with water, dried over sodium sulphate and run down under vacuum to give 1.7 g of crude product. Recrystallisation from toluene gave pure title product (1.3 g), mp 127°-129° C.

EXAMPLE 48

5-Cyano-2-acetoxy-2,3-dihydro-3,3-dimethylbenzofuran (I)

2-Chloro-5-cyano-2,3-dihydro-3,3-dimethylbenzofuran (2 g), prepared as in Example 45, was heated under reflux in glacial acetic acid (20 ml) for 3¼ hours. The solution was then added to ice/water and the product was separated by filtration and dried. The crude yield was 1.8 g. Recrystallisation from ethanol gave 1.6 g of title product, mp 138°-140° C.

EXAMPLE 49

5-Cyano-2-morpholino-2,3-dihydro-3,3-dimethylbenzofuran (I)

2-Chloro-5-cyano-2,3-dihydro-3,3-dimethylbenzofuran (4.1 g), prepared as in Example 45 was heated under reflux at about 130° C. in morpholine (20 ml) for 4 hours. Addition to ice-water, followed by extraction with diethyl ether, gave, after water washing, drying over sodium sulphate and running down, 3.3 g of crude title product. Recrystallisation from isopropanol gave 2.3 g of pure product, mp 105°-107° C.

Analysis: $C_{15}H_{18}N_2O_2$ requires: C, 69.74; H, 7.02; N, 10.85%. found: C, 69.94; H, 7.24; N, 11.26%.

EXAMPLES 50-53

Wettable powders were prepared by grinding together the following ingredients:

|  | Ex 50 | Ex 51 | Ex 52 | Ex 53 |
|---|---|---|---|---|
| Compound of Example 1 | 50% w/w | — | — | — |
| Compound of Example 2 | — | 50% w/w | — | — |
| Compound of Example 3 | — | — | 50% w/w | — |
| Compound of Example 10 | — | — | — | 50% w/w |
| Reax 45L (lignin based wetting and dispersing agent) | 5% w/w | 5% w/w | 5% w/w | 5% w/w |
| China clay | 45% w/w | 45% w/w | 45% w/w | 45% w/w |

All were stable on storage and were easily dispersible in water. for application. Similar formulations were also prepared containing each of the compounds of Examples 17, 22, 37, 40 and 41.

EXAMPLE 54

An emulsifiable concentrate was prepared by admixing the following ingredients:

|  | g/l |
|---|---|
| Compound of Example 5 | 250 |
| Arylan CA (70% ethanol solution of calcium dodecylbenzene sulphonate) | 25 |
| Ethylan C4OAH (ethylene oxide/castor oil condensation product) | 25 |
| Naphtha 2199 | to volume |

EXAMPLE A

The compounds of the Examples listed below, respectively formulated as attaclay/sand dusts were incorporated in John Innes I potting compost at a rate equivalent to 26 ppm weight/volume of active ingredient to soil and placed in anodised aluminium pans, 19 cm long×9.5 cm wide×5 cm deep. This rate is approximately equivalent to a soil surface application of 11.2 kg active ingredient/hectare cultivated to a depth of 5 cm. Seeds of peas, mustard, linseed, maize, oats and ryegrass were sown in the treated soil, watered and placed in a controlled environment room (22° C.; 65–85% R.H; 14 hours artificial illumination at 1200 foot candles) for 21 days. The plants were then visually assessed for any growth regulatory or herbicidal effects. All differences from an untreated control were noted as % reduction relative to the untreated control.

TABLE 1

| Ex No | Peas— Pisum sativum | Mustard— Sinapis alba | Linseed— Linum usitatis- simum | Maize— Zea mays | Oats— Avena sativa | Ryegrass— Lolium perenne |
|---|---|---|---|---|---|---|
| 1 | 90 | 90 | 90 | 80 | 100 | 100 |
| 2 | 70 | 90 | 90 | 100 | 90 | 100 |
| 3 | 90 | 100 | 90 | 100 | 100 | 100 |
| 5 | 90 | 80 | 80 | 5 | 100 | 90 |
| 9 | 90 | 100 | 90 | 80 | 100 | 100 |
| 10 | 90 | 90 | 90 | 70 | 100 | 100 |
| 11 | 75 | 60 | 70 | 80 | 90 | 15 |
| 12 | 80 | 70 | 80 | 90 | 100 | 25 |
| 15 | 90 | 90 | 90 | 100 | 100 | 100 |
| 16 | 90 | 100 | 90 | 100 | 90 | 90 |
| 17 | 90 | 90 | 80 | 90 | 100 | 80 |
| 18 | 90 | 90 | 90 | 100 | 100 | 90 |
| 19 | 90 | 100 | 90 | 90 | 100 | 100 |
| 20 | 95 | 100 | 80 | 100 | 100 | 100 |
| 21(I) | 90 | 100 | 80 | 100 | 100 | 90 |
| 21(VI) | 90 | 90 | 80 | 100 | 100 | 90 |
| 22 | 90 | 90 | 90 | 100 | 100 | 100 |
| 23 | 90 | 100 | 90 | 100 | 100 | 90 |
| 27 | 90 | 100 | 90 | 90 | 90 | 90 |
| 28 | 80 | 90 | 80 | 90 | 90 | 90 |
| 29 | 90 | 100 | 80 | 90 | 100 | 90 |
| 37 | 15 | 75 | 60 | 90 | 90 | 45 |
| 38 | 30 | 50 | 70 | 0 | 40 | 70 |
| 40 | 65 | 90 | 90 | 100 | 100 | 100 |
| 41 | 65 | 90 | 90 | 100 | 80 | 80 |
| 42 | 40 | 90 | 90 | 100 | 90 | 80 |

EXAMPLE B

Seeds of peas, mustard, linseed, ryegrass, sugarbeet and oats were sown in anodised aluminium pans, 19 cm long×9.5 cm wide×5 cm deep containing John Innes I potting compost. They were then watered and placed in a controlled environment room (22° C.; 65–85% R.H; 14 hours illumination at 1200 foot-candles). 14 days after sowing, the seedlings received a foliar spray of the compounds of the Examples listed below respectively formulated as an aqueous suspension together with 1000 ppm of the wetting agent Lissapol NX. The concentration of active ingredient and volume of application were adjusted so as to be equivalent to a rate of 2.8 kg/ha in 450 liters per hectare. After seven days growth in a controlled environment room the plants were visually assessed for any herbicidal or growth regulant response. All differences from the untreated control were noted as % reduction relative to the untreated controls.

TABLE 2

| Ex No | Peas— Pisum sativum | Mustard— Sinapis alba | Linseed— Linum usitatis- simum | Ryegrass— Lolium perenne | Oats— Avena sativa | Sugar- beet— Beta vulgaris | French beans— Phaseolus vulgaris |
|---|---|---|---|---|---|---|---|
| 1 | 70 | 5 | 5 | 30 | 40 | 30 | — |
| 2 | 60 | 80 | 70 | 80 | 70 | 40 | 40 |
| 3 | 70 | 90 | 60 | 80 | 70 | 80 | 5 |
| 9 | 60 | 90 | 80 | 90 | 70 | 70 | — |
| 10 | 60 | 100 | 70 | 90 | 80 | 70 | — |
| 11 | 5 | 25 | 5 | 5 | 5 | 30 | 5 |
| 12 | 40 | 10 | 10 | 40 | 40 | 5 | 0 |
| 15 | 30 | 70 | 40 | 60 | 50 | 60 | 35 |
| 16 | 40 | 30 | 30 | 5 | 5 | 25 | 20 |
| 17 | 30 | 40 | 50 | 60 | 30 | 25 | 40 |
| 18 | 50 | 40 | 30 | 50 | 70 | 15 | 40 |
| 19 | 40 | 60 | 40 | 50 | 50 | 40 | 65 |
| 20 | 40 | 30 | 30 | 50 | 40 | 20 | 70 |
| 21(I) | 30 | 40 | 40 | 50 | 60 | 35 | 40 |
| 21(VI) | 30 | 50 | 30 | 70 | 40 | 15 | 15 |
| 22 | 60 | 50 | 40 | 70 | 70 | 70 | 30 |
| 23 | 25 | 25 | 20 | 60 | 50 | 25 | 30 |
| 26 | 40 | 80 | 60 | 90 | 60 | 40 | — |
| 27 | 30 | 30 | 30 | 30 | 40 | 20 | 5 |
| 28 | 5 | 30 | 30 | 30 | 5 | 0 | 0 |
| 29 | 5 | 0 | 20 | 15 | 5 | 20 | 0 |
| 37 | 5 | 30 | 40 | 50 | 60 | 20 | 65 |
| 38 | 20 | 10 | 0 | 0 | 15 | 25 | 0 |
| 40 | 15 | 75 | 25 | 70 | 70 | 5 | 45 |
| 41 | 5 | 30 | 15 | 60 | 50 | 5 | 15 |
| 42 | 15 | 30 | 25 | 60 | 50 | 5 | 5 |

EXAMPLE C

The compounds of the Examples listed below respectively were formulated as (I) attaclay/sand dusts and incorporated in John Innes I potting compost at a rate equivalent to 6.5 weight/volume of active ingredient to soil and placed in anodised aluminium pans, 19 cm long×9.5 cm wide×5 cm high. These are respectively approximately equivalent to a surface applications of 2.8 and 1.4 kg active ingredient per hectare cultivated to a depth of 5 cm. Seeds of the species listed below were sown in the treated soil, one species per pan, watered and placed in a controlled environment room (22° C.; 65-85% R.H. and 14 hours artificial illumination at 1600 foot candles) for 21 days; (II) aqueous suspensions together with 1000 ppm of the wetting agent Lissapol NX. The surfaces of an additional set of pans with seeds already sown were then sprayed with 2.8 and 1.4 kg/ha in 450 liters/hectare. The plants were then visually assessed for any growth regulatory or herbicidal effects.

All differences from an untreated control were noted as % reduction relative to the untreated control.

TABLE 3

(I) - Soil incorporation

| Ex No | Sugar beet (Beta vulgaris) | Chickweed (Stellaria media) | Mustard (Sinapis alba) | Cotton (Cossypium spp) | Tomato (Lycopersicon esulentum) | Fathen (Chenonpodium album) | Carrot (Daucus carota) | Wheat (Triticum aestivum) | Barley (Hordeum vulgare) | Wild Oat (Avena fatua) | Blackgrass (Alopecurus myosuroides) | Barnyardgrass (Echinochloa crusgalli) | Crabgrass (Digitaria sunguinalis) |
|---|---|---|---|---|---|---|---|---|---|---|---|---|---|
| 1 | — | 70 | 80 | 40 | 70 | 80 | 20 | 20 | 90 | 90 | 90 | 0 | 70 |
| 2 | 20 | 90 | 80 | 40 | 80 | 90 | 90 | 90 | 70 | 90 | 100 | 80 | 100 |
| 3 | 70 | 100 | 80 | 70 | 80 | 100 | 80 | 90 | 80 | 90 | 100 | 90 | 100 |
| 5 | — | — | — | — | — | — | — | 80 | 60 | 100 | 50 | — | 100 |
| 9 | — | 100 | 90 | 60 | 90 | 100 | 80 | 80 | 60 | 90 | 80 | — | 100 |
| 10 | — | 100 | 80 | 40 | 90 | 100 | 80 | 90 | 80 | 100 | 90 | — | 100 |
| 11 | 75 | 70 | 40 | 25 | 70 | 60 | 10 | 80 | 25 | 100 | 100 | 0 | 90 |
| 12 | 50 | 40 | 40 | 35 | 80 | 80 | 0 | 70 | 20 | 100 | 90 | 15 | 100 |
| 15 | 80 | 100 | 70 | 50 | 80 | 80 | 80 | 90 | 70 | 100 | 100 | 90 | 100 |
| 16 | — | — | — | — | — | — | — | 90 | 60 | 70 | 90 | 80 | 90 |
| 17 | 90 | 100 | 80 | 70 | 90 | 100 | 70 | 90 | 65 | 90 | 100 | 90 | 100 |
| 18 | 85 | 100 | 100 | 75 | 90 | 100 | 90 | 80 | 70 | 100 | 100 | 90 | 100 |
| 19 | 80 | 90 | 70 | 60 | 90 | 90 | 70 | 80 | 60 | 90 | 100 | 80 | 90 |
| 20 | 80 | 100 | 90 | 60 | 90 | 90 | 80 | 70 | 70 | 80 | 90 | 90 | 90 |
| 21(I) | 80 | 100 | 70 | 60 | 80 | 80 | 70 | — | — | — | — | — | — |
| 21(VI) | 70 | 100 | 70 | 60 | 80 | 80 | 70 | — | — | — | — | — | — |
| 22 | 85 | 100 | 70 | 70 | 90 | 90 | 90 | 90 | 70 | 80 | 100 | 90 | 100 |
| 23 | — | — | — | — | — | — | — | 90 | 80 | 90 | 90 | 80 | 100 |
| 26 | — | 100 | 80 | 40 | 90 | 100 | 80 | 90 | 90 | 90 | 90 | — | 100 |
| 27 | 80 | 90 | 70 | 50 | 90 | 80 | 80 | 80 | 60 | 90 | 90 | 90 | 90 |
| 28 | 70 | 90 | 70 | 50 | 80 | 80 | 70 | 90 | 50 | 90 | 90 | 80 | 90 |
| 29 | 70 | 100 | 70 | 50 | 80 | 80 | 70 | 90 | 60 | 70 | 90 | 70 | 90 |
| 37 | — | — | — | — | — | — | — | 55 | 35 | 100 | 100 | 90 | 90 |
| 40 | 0 | 50 | 80 | 40 | 80 | 10 | 40 | 90 | 70 | 100 | 100 | 80 | 100 |
| 41 | 50 | 90 | 80 | 40 | 90 | 90 | 90 | 90 | 70 | 100 | 100 | 80 | 100 |
| 42 | 60 | 100 | 100 | 60 | 90 | 100 | 100 | 90 | 70 | 90 | 100 | 70 | 90 |

TABLE 4

(II) - Surface Spray (2.8 Kg/ha)

| Ex No | Sugar beet | Chickweed | Mustard | Cotton | Tomato | Fathen | Carrots | wheat | Barley | Wild Oats | Blackgrass | Barnyardgrass | Crabgrass |
|---|---|---|---|---|---|---|---|---|---|---|---|---|---|
| 1 | — | 60 | 90 | 20 | 80 | 90 | 20 | 20 | 80 | 90 | 90 | 0 | 80 |
| 2 | 20 | 90 | 80 | 40 | 90 | 100 | 90 | 90 | 60 | 100 | 100 | 100 | 100 |
| 3 | 70 | 100 | 70 | 60 | 90 | 100 | 90 | 90 | 70 | 100 | 100 | 90 | 100 |
| 5 | — | — | — | — | — | — | — | 60 | 30 | 100 | 30 | — | 100 |
| 9 | — | 100 | 90 | 30 | 90 | 100 | 90 | 90 | 60 | 100 | 100 | — | 100 |
| 10 | — | 100 | 90 | 30 | 90 | 100 | 90 | 90 | 60 | 100 | 90 | — | 100 |
| 11 | 40 | 80 | 40 | 0 | 50 | 60 | 0 | 25 | 0 | 90 | 90 | 100 | 100 |
| 12 | 70 | 70 | 40 | 0 | 70 | 80 | 0 | 35 | 0 | 90 | 90 | 20 | 100 |
| 15 | 70 | 90 | 70 | 40 | 80 | 80 | 80 | 90 | 65 | 100 | 100 | 100 | 100 |
| 16 | — | — | — | — | — | — | — | 60 | 40 | 60 | 90 | 50 | 100 |
| 17 | 100 | 100 | 100 | 60 | 90 | 100 | 90 | 90 | 55 | 90 | 90 | 100 | 100 |
| 18 | 75 | 100 | 90 | 55 | 90 | 90 | 80 | 100 | 70 | 100 | 100 | 100 | 100 |
| 19 | 70 | 90 | 60 | 40 | 80 | 90 | 70 | 70 | 50 | 90 | 100 | 85 | 100 |
| 20 | 80 | 100 | 60 | 40 | 90 | 90 | 80 | 70 | 40 | 90 | 100 | 90 | 100 |
| 21(I) | 80 | 100 | 70 | 30 | 80 | 80 | 70 | — | — | — | — | — | — |
| 21(VI) | 60 | 80 | 70 | 30 | 80 | 80 | 80 | — | — | — | — | — | — |
| 22 | 75 | 100 | 90 | 40 | 90 | 100 | 80 | 80 | 55 | 90 | 100 | 80 | 100 |
| 23 | — | — | — | — | — | — | — | 80 | 40 | 90 | 100 | 100 | 100 |
| 26 | — | 100 | 90 | 30 | 90 | 100 | 90 | 90 | 70 | 100 | 80 | — | 100 |
| 27 | 70 | 90 | 60 | 20 | 80 | 80 | 80 | 70 | 50 | 100 | 100 | 75 | 90 |
| 28 | 60 | 90 | 50 | 30 | 80 | 80 | 70 | 60 | 40 | 80 | 100 | 50 | 90 |
| 29 | 70 | 100 | 70 | 50 | 80 | 70 | 70 | 70 | 50 | 80 | 100 | 50 | 90 |
| 40 | 5 | 80 | 80 | 25 | 80 | 40 | 40 | 90 | 60 | 100 | 90 | 100 | 100 |
| 41 | 30 | 100 | 90 | 0 | 90 | 90 | 90 | 80 | 55 | 100 | 100 | 100 | 100 |
| 42 | 30 | 100 | 90 | 0 | 90 | 90 | 90 | 90 | 50 | 80 | 100 | 100 | 100 |

TABLE 5

(III) - Surface Spray (0.7 Kg/ha)

| Ex No | Wheat | Barley | Wild Oats | Black-grass | Barn-yard-grass | Crab-grass | Yellow Nut-Sedge (Cyperus esculentus) |
|---|---|---|---|---|---|---|---|
| 1 | 20 | 70 | 90 | 70 | 20 | 80 | — |
| 2 | 40 | 0 | 100 | 100 | 90 | 90 | — |
| 3 | 20 | 20 | 90 | 90 | 30 | 90 | — |
| 11 | 20 | 5 | 40 | 90 | 50 | 70 | 30 |
| 12 | 0 | 0 | 80 | 80 | 0 | 90 | 30 |
| 15 | 10 | 0 | 80 | 80 | 0 | 90 | 40 |
| 16 | 70 | 40 | 90 | 100 | 80 | 100 | — |
| 17 | 30 | 5 | 95 | 95 | 70 | 90 | 90 |
| 18 | 40 | 40 | 80 | 90 | 60 | 90 | 70 |
| 19 | 40 | 10 | 90 | 95 | 60 | 90 | 90 |
| 20 | 20 | 0 | 70 | 90 | 0 | 90 | 50 |
| 21(I) | 20 | 20 | 70 | 95 | 0 | 90 | 50 |
| 21(VI) | 50 | 40 | 70 | 95 | 0 | 90 | 70 |
| 22 | 40 | 20 | 95 | 95 | 90 | 90 | 90 |
| 23 | 30 | 5 | 70 | 90 | 0 | 90 | 70 |
| 26 | | | | | | | |
| 27 | 30 | 0 | 40 | 90 | 50 | 90 | 70 |
| 28 | 70 | 20 | 90 | 90 | 20 | 100 | — |
| 29 | 0 | 0 | 90 | 95 | 0 | 90 | 70 |
| 37 | 20 | 10 | 90 | 90 | 90 | 90 | 30 |
| 40 | 20 | 5 | 90 | 95 | 80 | 80 | 0 |
| 41 | 40 | 0 | 95 | 95 | 80 | 90 | 70 |
| 42 | 20 | 10 | 90 | 95 | 60 | 80 | 20 |

EXAMPLE D

Seeds of wheat, barley, wild oats, blackgrass, barnyardgrass and crabgrass were sown in anodised aluminium pans, 19 cm long×9.5 cm wide×5 cm deep containing John Innes I potting compost. They were then watered and placed in a controlled environment room (22° C.; 65-85% R.H; 14 hours artificial illumination at 1200 foot candles). Fourteen days after sowing, the seedlings received a foliar spray of one of the compounds of Example 1, 2, 3, 9, 10 or 26 formulated as an aqueous suspension together with 1000 ppm of the wetting agent Lissapol NX (nonyl phenol condensed with ethylene oxide). The concentration of active ingredient and volume of application was adjusted so as to be equivalent to a rate of 2.8 or 1.4 kg/ha in 450 liters per hectare. After seven days growth in a controlled environment room the plants were visually assessed for any herbicidal or growth regulant response. All differences from the untreated control were scored according to a herbicidal index where 0=no effect and 9=complete kill. The results are summarised in the following table:

| Species | Compound | | | | | |
|---|---|---|---|---|---|---|
| | Ex 1 2.8kg | Ex 2 2.8kg | Ex 3 2.8kg | Ex 10 2.8kg | Ex 9 2.8kg | Ex 26 2.8kg |
| Wheat (Triticum aestivum) | 1 | 6 | 7 | 7 | 6 | 5 |
| Barley (Hordeum vulgare) | 4 | 4 | 5 | 4 | 3 | 3 |
| Wild Oats (Avena fatua) | 5 | 6 | 7 | 7 | 6 | 5 |
| Blackgrass (Alopecurus myosuroides) | 6 | 8 | 8 | 9 | 8 | 7 |
| Barnyardgrass (Echinochloa crus-galli) | 1 | 6 | 7 | 7 | 5 | 6 |
| Crabgrass (Digitaria sanguinalis) | 6 | 8 | 8 | 7 | 7 | 7 |

We claim:

1. A 2,3-dihydro-5-cyanobenzofuran of the formula:

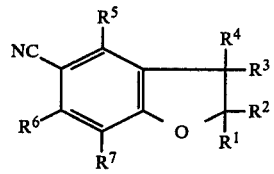

wherein $R^1$ represents hydrogen and $R^2$ represents hydrogen, hydroxy, alkoxy, unsubstituted alkanoyloxy, alkanoyloxy substituted by one or more hydroxy, alkoxy, alkylthio or halogen groups, benzoyloxy, alkenoyloxy, carbamoyloxy, alkylcarbamoyloxy, phenylcarbamoyloxy, dialkylcarbamoyloxy, alkylsulphonyloxy, alkoxycarbonyloxy, alkylthiocarbonyloxy, halogen, isothiocyanato, amino, alkylamino, dialkylamino, phenylamino, unsubstituted alkanoylamino, alkanoylamino substituted on the alkanoyl group by one or more hydroxy, alkoxy, alkylthio or halogen groups, benzoylamino, alkenoylamino, carbamoylamino, alkylcarbamoylamino, phenylcarbamoylamino, dialkylcarbamoylamino, alkylsulphonylamino, alkoxycarbonylamino, alkylthiocarbonylamino, cyano or alkylthio, any alkyl moiety in the group $R^2$ being of 1 to 6 carbon atoms and any alkenyl moiety in the group $R^2$ being of 2 to 6 carbon atoms; $R^3$ and $R^4$ each represents hydrogen or alkyl of 1 to 6 carbon atoms; and $R^5$, $R^6$ and $R^7$, which may be the same or different, each represent hydrogen, halogen, alkyl of 1 to 6 carbon atoms, alkoxy of 1 to 6 carbon atoms, alkanoyl of 2 to 6 carbon atoms or cyano.

2. A compound according to claim 1 wherein $R^1$ represents hydrogen and $R^2$ represents hydrogen, hydroxy, methoxy, ethoxy, n-propoxy, isopropoxy, n-butoxy, isobutoxy, acetoxy, chloroacetoxy, propanoyloxy, n-butanoyloxy, n-pentanoyloxy, isobutanoyloxy, isopentanoyloxy, amino, methylamino, dimethylamino, phenylamino, acetylamino, propionylamino, methylsulphonylamino, N-methyl-N-sulphonylamino, ureido, 3-methylureido, 3,3-dimethylureido, 1,3,3-trimethylureido, methoxycarbonyloxy, methylthiocarbonyloxy, methoxycarbonylamino, methylthiocarbonylamino, propenoyloxy, methylcarbamoyloxy, dimethylcarbamoyloxy, methylsulphonyloxy, chlorine, bromine, iodine, isothiocyanato, cyano, methylthio or ethylthio.

3. A compound according to claim 1 where $R^3$ and $R^4$ both represent methyl.

4. A compound according to claim 1 wherein $R^5$, $R^6$ and $R^7$ each represent hydrogen.

5. A compound which is:
5-cyano-2,3-dihydro-3,3-dimethylbenzofuran,
5-cyano-2,3-dihydro-3,3-dimethyl-2-hydroxybenzofuran,
5-cyano-2,3-dihydro-3,3-dimethyl-2-methoxybenzofuran,
5-cyano-2,3-dihydro-3,3-dimethyl-2-ethoxybenzofuran,
5-cyano-2,3-dihydro-3,3-dimethyl-2-n-propoxybenzofuran,
5-cyano-2,3-dihydro-3,3-dimethyl-2-isopropoxybenzofuran,
5-cyano-2,3-dihydro-3,3-dimethyl-2-isobutoxybenzofuran,
5-cyano-2,3-dihydro-3,3-dimethyl-2-acetoxybenzofuran, 5-cyano-2,3-dihydro-3,3-dimethyl-2-propionyloxybenzofuran,
5-cyano-2,3-dihydro-3,3-dimethyl-2-n-butyryloxybenzofuran,
5-cyano-2,3-dihydro-3,3-dimethyl-2-isobutyryloxybenzofuran,
5-cyano-2,3-dihydro-3,3-dimethyl-2-n-valeroyloxybenzofuran,
5-cyano-2,3-dihydro-3,3-dimethyl-2-isovaleroyloxybenzofuran,
5-cyano-2,3-dihydro-3,3-dimethyl-2-chloroacetoxybenzofuran,
5-cyano-2,3-dihydro-3,3-dimethyl-2-acryloyloxybenzofuran,
5-cyano-2,3-dihydro-3,3-dimethylbenzofuran-2-yl N-methylcarbamate,
5-cyano-2,3-dihydro-3,3-dimethylbenzofuran-2-yl N-phenylcarbamate,
5-cyano-2,3-dihydro-3,3-dimethyl-2-chlorobenzofuran, or
5-cyano-2,3-dihydro-3,3-dimethyl-2-isothiocyantobenzofuran.

6. A herbicidal composition which comprises from 0.5 to 99% by weight of one or more compounds according to claim 2, 3, 4, 5 or 1 in association with a suitable carrier and/or surface active agent.

7. A method of combating weeds at a locus infested or liable to be infested with them, which method comprises applying to the locus a herbicidally effective amount of one or more compounds according to claim 2, 3, 4, 5 or 1.

* * * * *